US011510998B2

(12) United States Patent
Venditti et al.

(10) Patent No.: US 11,510,998 B2
(45) Date of Patent: Nov. 29, 2022

(54) GENE THERAPY FOR COMBINED METHYLMALONIC ACIDEMIA/ACIDURIA AND HYPERHOMOCYSTEINEMIA/ HOMOCYSTINURIA, COBALAMIN C TYPE, AND DEFICIENCY OF MMACHC

(71) Applicant: The United States of America, as represented by the Secretary, Department of Health and Human Services, Bethesda, MD (US)

(72) Inventors: Charles P. Venditti, Potomac, MD (US); Jennifer L. Sloan, Silver Spring, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 730 days.

(21) Appl. No.: 16/061,091

(22) PCT Filed: Apr. 27, 2016

(86) PCT No.: PCT/US2016/029512
§ 371 (c)(1),
(2) Date: Jun. 11, 2018

(87) PCT Pub. No.: WO2017/099838
PCT Pub. Date: Jun. 15, 2017

(65) Prior Publication Data
US 2018/0353623 A1 Dec. 13, 2018

Related U.S. Application Data

(60) Provisional application No. 62/279,285, filed on Jan. 15, 2016, provisional application No. 62/266,352, filed on Dec. 11, 2015.

(51) Int. Cl.
*C12N 15/00* (2006.01)
*A61K 39/002* (2006.01)
*A61K 48/00* (2006.01)
*C07K 14/435* (2006.01)
*A61P 43/00* (2006.01)
*A61K 47/26* (2006.01)
*C12N 15/67* (2006.01)
*C12N 15/85* (2006.01)

(52) U.S. Cl.
CPC .......... *A61K 48/0066* (2013.01); *A61K 47/26* (2013.01); *A61P 43/00* (2018.01); *C07K 14/435* (2013.01); *C12N 15/67* (2013.01); *C12N 15/85* (2013.01); *C12N 2750/14143* (2013.01)

(58) Field of Classification Search
CPC ..... A61K 48/0066; A61K 47/26; A61P 43/00; C07K 14/435; C12N 15/67; C12N 15/85
See application file for complete search history.

(56) References Cited

U.S. PATENT DOCUMENTS

| 8,293,187 | B2 | 10/2012 | Venditti et al. | |
|---|---|---|---|---|
| 8,721,988 | B2 | 5/2014 | Venditti | |
| 2014/0147432 | A1* | 5/2014 | Bancel | A61K 38/17 424/94.64 |
| 2014/0155468 | A1* | 6/2014 | Gregory | A61P 13/12 514/44 R |
| 2014/0364338 | A1 | 12/2014 | Schaffer et al. | |
| 2016/0040150 | A1* | 2/2016 | Venditti | A61K 48/0066 514/44 R |

FOREIGN PATENT DOCUMENTS

| DE | 10 2013 010 253 B3 | 2/2014 | |
|---|---|---|---|
| WO | WO 2011/044927 A1 | 4/2011 | |
| WO | WO 2012/145601 A3 | 10/2012 | |
| WO | WO 2014/089212 A1 | 6/2014 | |
| WO | WO 2014/143884 A2 | 9/2014 | |
| WO | WO-2014143884 A2 * | 9/2014 | ............... C12N 9/90 |
| WO | WO 2016/164642 A1 | 10/2016 | |
| WO | WO 2016/172574 A2 | 10/2016 | |

OTHER PUBLICATIONS

Loewy et al., "Epigenetic modification of the gene for the vitamin B12 chaperone MMACHC can result in increased tumorigenicity and methionine dependence", 2009, Molecular Genetics and Metabolism 96, p. 261-267.*
Lerner-Ellis, "Identification of the gene responsible for methylmalonic aciduria and homocystinuria, cbIC type", 2006, Nature Genetics 38(1), p. 93-100.*
Pearson et al., "An Introduction to Sequence Similarity ("Homology") Searching", 2013, Current Protocols in Bioinformations, p. 1-9.*
Homocystinuria—Wikipedia pp. 1-6; downloaded Oct. 8, 2021.*
Methylmalonic acidemia—Wikipediapp. 1-12; downloaded Oct. 8, 2021.*
Ngo, in the Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*

(Continued)

*Primary Examiner* — Maria G Leavitt
(74) *Attorney, Agent, or Firm* — Leydig, Voit & Mayer, Ltd.

(57) ABSTRACT

The present invention provides a synthetic MMACHC polynucleotide comprising a polynucleotide encoding MMACHC that is codon-optimized for expression in a human. Also provided is a polypeptide encoded by a synthetic MMACHC polynucleotide, an expression vector comprising a MMACHC gene sequence under the control of a chicken beta actin (CBA) promoter, and an expression vector comprising a synthetic MMACHC polynucleotide. Methods of treating cobalamin C deficiency and for detecting or tracking exogenous MMACHC are also provided.

14 Claims, 20 Drawing Sheets
Specification includes a Sequence Listing.

(56) References Cited

OTHER PUBLICATIONS

Arnold et al., "PgmNr 379: A mouse model of cbIC deficiency displays reduced survival, growth retardation, and combined methylmalonic academia and hyperhomocysteinemia," ASHG abstract, 1 page (Oct. 6, 2015).
Arnold et al., "A novel mouse model of cbIC deficiency recapitulates the human phenotype and exhibits improved survival following neonatal AAV gene therapy," National Human Genome Research Institute, Poster, 1 page (Apr. 30, 2015).
Arnold et al., "A novel mouse model of cbIC deficiency displays reduced survival, growth retardation, and combined methylmalonic academia and hyperhomocysteinemia," Powerpoint presentation, ASHG Oct. 10, 2015, 22 pages.
Brooks et al., "Ophthalmic Manifestations and Long-Term Visual Outcomes in Patients with Cobalamin C Deficiency," *Ophthalmology* 123(3): 571-582 (Mar. 2016) author manuscript.
Carrillo-Carrasco et al., "Combined methylmalonic acidemia and homocystinuria, cbIC type. II. Complications, pathophysiology, and outcomes," *J Inherit Metab Dis.* 35(1):103-114 (2012) author manuscript.
Carrillo-Carrasco et al., "Hydroxocobalamin dose escalation improves metabolic control in cbIC," *J Inherit Metab Dis* 32(6): 728-731 (Dec. 2009) author manuscript.
Chandler et al., "Adeno-associated virus serotype 8 gene transfer rescues a neonatal lethal murine model of propionic academia," *Human Gene Therapy* 22:477-481 (Apr. 2011).
Chandler et al., "Adenoviral-mediated correction of methylmalonyl-CoA mutase deficiency in murine fibroblasts and human hepatocytes," *BMC Med Genet.* 8(24): pp. 1-10 (2007).
Chandler et al., "Mitochondrial dysfunction in mut methylmalonic academia," *FASEB J.*,23(4): 1252-1261 (2009).
Chandler et al., "Liver-directed adeno-associated virus serotype 8 gene transfer rescues a lethal murine model of citrullinemia Type 1," *Gene Ther.* 20(12): 9 pages (Dec. 2013) author manuscript.
Chandler et al., "Long-term rescue of a legal murine model of methylmalonic academia using Adeno-associated viral gene therapy," *Mol Ther.* 18:11-16 (2010) author manuscript.
Chandler et al., "Pre-clinical efficacy and dosing of an AAV8 vector expressing methylmalonyl-CoA mutase in a murine model of methylmalonic academia (MMA)," *Mol Genet Metab.* 107(3): 617-619 (Nov. 2012).
Cusmano-Ozog, "Cobalamin C disease identified by expanded newborn screening: The California Experience," SIMD Abstracts, *Molecular Genetics and Metabolism* 90:240 (2007).
Dalkara et al., "In vivo-directed evolution of a new adeno-associated virus for therapeutic outer retinal gene delivery from the vitreous," *Sci Trans Med* 12(5): 189ra76 (Jun. 12, 2013), 11 pages.
International Preliminary Report on Patentability, PCT/US2016/029512, 7 pages, dated Jun. 21, 2018.
International Search Report, PCT/US2016/029512, dated Jun. 28, 2016, 5 pages.
Kay et al., "Targeting photoreceptors via intravitreal delivery using novel, capsid-mutated AAV vectors," *PLoS One*, 8(4): pp. 1-12 (2013), with erratum.
Lerner-Ellis et al., "Identification of the gene responsible for methylmalonic aciduria and homocystinuria, cbIC type," *Nat. Genet.* 38:93-100 (2006).
Markusic et al., "High-efficiency transduction and correction of murine hemophilia B using AAV2 vectors devoid of multiple surface-exposed tyrosines," *Mol Ther.*, 18(12): 2048-2056 (2010).
Martinelli et al., "Cobalamin C defect: natural history, pathophysiology, and treatment," *J Inherit Metab Dis*, 34(1):127-135 (2011).

Petrs-Silva et al, "High-efficiency transduction of the mouse retina by tyrosine-mutant AAV serotype vectors," *Mol Ther.*, 17(3): 463-471 (2009).
Profitlich et al., "High prevalence of structural heart disease in children with cbIC-type methylmalonic aciduria and homocystinuria," *Molecular Genetics and Metabolism* 98:344-348 (2009).
Qiao et al., "Adeno-associated virus serotype 6 capsid tyrosine-to-phenylalanine mutations improve gene transfer to skeletal muscle," *Hum Gene Ther.*, 21(10):1343-1348 (2010).
Qiao et al., "Single tyrosine mutation in AAV8 and AAV9 capsids is insufficient to enhance gene delivery to skeletal muscle and heart," *Hum Gene Ther Methods*, 23(1): 29-37 (2012).
Ryals et al., "Quantifying transduction efficiencies of unmodified and tyrosine capsid mutant AAV vectors in vitro using two ocular cell lines," *Mol Vis.*, 17:1090-1102 (2011).
Sanders, "Researchers develop easy and effective therapy to restore sight," Berkeley News, 5 pages (Jun. 12, 2013).
Sloan et al., "A A mouse model of cbIC deficiency created by genome editing recapitulates the human phenotype," poster, NHGRI Symposium, 1 page, dated Dec. 9, 2014.
Sloan et al., "A mouse model of cbIC deficiency created by genome editing recapitulates the phenotype in humans: failure to thrive, biochemical abnormaillies, and reduced survival," Abstract, 2014 NHGRI Symposium, p. 9, (Dec. 11-12, 2014).
Human MMACHC AAV (adeno-associated virus), Vector Biolabs, www.vectorbiolabs.com, 1 page, accessed Nov. 16, 2015.
Vector catalog of the Perelman School of Medicine at the University of Pennsylvania, 9 pages, dated Nov. 13, 2013.
Weisfeld-Adams et al., "Newborn screening and early biochemical follow-up in combined methylmalonic aciduria and homocystinuria, cbIC type, and utility of methionine as a secondary screening analyte," *Mol Genet Metab.* 99(2): 116-123 (Feb. 2010) author manuscript.
Written Opinion of the International Searching Authority, PCT/US2016/029512, dated Jun. 28, 2016, 5 pages.
Yu et al., "An X-linked cobalamin disorder caused by mutations in transcriptional coregulator HCFC1," *Am J Hum Genet.*, 93(3): 506-514 (2013).
Barzel et al., "Promoterless gene targeting without nucleases ameliorates haemophilia B in mice," *Nature*, 577(7534), 360-364 (2015), published online Oct. 29, 2014, Author manuscript as published in PubMed.
Bogner et al., "Capsid mutated adeno-associated virus delivered to the anterior chamber results in efficient transduction of a trabecular meshwork in mouse and rat," *PLoS One*, 10(6), e0128759, 16 pp. (Jun. 8, 2015).
Han et al., "Clinical presentation, gene analysis and outcomes in young patients with early-treated combined methylmalonic academia and homocysteinemia (cbIC type) in Shandong province, China," *Brain Dev.*, 38(5), 491-497 (2016), published online Nov. 10, 2015.
Moreno-Garcia et al., "The Mmachc gene is required for pre-implantation embryogenesis in the mouse," *Mol Genet Metab.*, 112(3), 198-204 (2014), published online May 14, 2014.
Santiago-Ortiz et al., "AAV ancestral reconstruction library enables selection of broadly infectious viral variants," *Gene Ther.*, 22(12), 934-946 (2015), published online Jul. 17, 2015, Author manuscript as published in PubMed.
Wang et al., "Homology-driven genome editing in hematopoietic stem and progenitor cells using zinc finger nuclease mRNA and AAV6 donors," *Nat Biotechnol.*, 33(12), 1256-1263 (2015), published online Nov. 9, 2015, Author manuscript as published in PubMed.
Zinn et al., "In silico reconstruction of the viral evolutionary lineage yields a potent gene therapy vector," *Cell Rep.*, 12(6), 1056-1068 (2015), published online Jul. 30, 2015, Author manuscript as published in PubMed.

\* cited by examiner

Figure 1A

```
ATGGAGCCGAAAGTCGCAGAGCTGAAGCAGAGAAGATCGAGGACACGCTATGTCCTTTTGGC    60
|||||||| ||||||||||||||||||||||||||||||||||||||||||||||||||||
ATGGAACCTAAAGTCGCAGAACTCAAGCAGAGAAGATCGAGGACACCCTGTGCCCGTTCGGA    60

TTCGAGGTTTACCCCTTCCAGGTGGCATGGTACAATGAACTCTTGCCTCCAGCCTTCCAC   120
||||||||||||| || ||||||||| ||||||| |||||| || |||||||| |||||
TTCGAGGTGTACCCTTTCCAAGTGGCCTGGTACAACGAGCTCCTGCCCCTGCTTTCCAT    120

CTACCGCTGCCAGGACCTACCCTGGCCTTCCTGGTACT-CAGCACGCCTGCCATGTTTGA   179
|| || ||||||||| | || ||||| |||| ||| || |||||| ||| || ||||||
TTGCCACTGCCCGGTCCGACTCTCGCGTTCTTGTGCTGTCG-ACCCCGCGATGTTCGA   179

CCGGGCCCCTCAAGCCCCTTCTTGCAGAGC-TGCCACCTCCGAATGCTGACTGACCCAGTGG   238
|||| || |||||||| |||| ||||| |  ||||| ||| |||||||||||||  || ||
CCGCGCCCTCAAGCCGTTCCTGCA-ATCATGTCATCTGCGGATGCTGACCGATCCGGTCG   238

ACCAGTGTGTGGCCTACCATCTGGGCCGTGTTAGAGAGAGCCTCCCAGAGCTGCAGATAG   298
|||||| | ||||| ||||| ||| || || |||||| ||| |||||| || ||||| |
ATCAGTGCGTGGCCTACCACCTGGGTCGCGTCAGGGAATCCCTGCCGGAGCTTCAGATCG   298

AAATCATTGCTGACTACGAGGTGCACCCCCAAGATCCTGGCCCCAGACAG   358
||| ||| || || ||| || ||||||  ||||| ||||| ||||| ||
AGATCATCGCGGATTACGAAGTGCACCCCAAAACCGGCGGCCCAAGATTCTCGCCCAAACCG   358

CAGCCCATGTAGCTGGGCTGCTTACTACTACCAACGACAAGATGTGGAGGCTGACCCAT   418
|| ||| | || |||||| ||| ||| |||| |||| ||| |||| ||||| |||| ||
CCGCGCACGTGGCTGGCTGCCGCCCTATTACTACCAGCGCCAGGACGTCGAGGCGGACCCTT   418

GGGGGAACCAGCGCATATCAGGTGTGTGCATACACCCCCGATTTGGGGCTGGTTTGCCA   478
|||| ||||||| |||| ||||||||||||| ||||| |||| ||||| |||| ||||
GGGCAATCAGAGAATCTCTGGAGTGTGCATCCACCCACGGTTCGGGGGATGGTTCGCAA   478
```

Figure 1B

```
TCCGAGGGGTAGTGCTGCTGCCAGGGATAGAGGTGCCAGATCTGCCACCCAGAAAACCTC  538
        ---------------------------------------------------
TTCGGGGCGTGGTGCTGCTGCCGGGAATCGAGGTGCCAGACTTGCCTCCTGAAAGCCCC    538

ATGACTGTGTACCTACAAGAGCTGACCGTATCGCCCCTACTCGAAGGCTTCAATTTCCACT  598
        ---------------------------------------------------
ACGACTGCGTGCCAACTAGAGCCGATAGAATTGCCCTGCTGGAAGGGTTCAACTTCCATT  598

GGCGTGATTGGACTTACCGGGATGCTGTGACACCCAGGAGCGCTACTCAGAAGAGCAGA   658
        ---------------------------------------------------
GGCGCGACTGGACCTACCGGGACGCTGTGACTCCTCAAGAACGCTACAGCGAAGAACAGA  658

AGGCCTACTTCTCCACTCTGCCCAACGATTGGCCCTATTGGGCTTGGCTCAGCCCT      718
        ---------------------------------------------------
AGGCCTACTTTTCAACTCCGCCCGGCCTGGCACTCCTGGGACTGGCCCAGCCCT       718

CAGAGAAGCCTAGTTCTCCCCTGGACCTTCCCTTTACCACACCCGCCCCCAAGAAGC    778
        ---------------------------------------------------
CCGAGAAGCCTAGCTCCCCCTCGCCCGGACTTGCCCTTCACCACCCCGGCCCCCAAAAAGC  778

CTGGGAATCCCAGCAGAGCCCGGAGCTGGCTCAGCCCCCAGGGTCTCACCACCTGCATCCC 838
        ---------------------------------------------------
CCGGCAACCCTAGCGGGCCAGTTCCTGCTGTGTCCTGGCTGTGTCCCCGAGGGGTGTCCC  838

CTGGCCCT   846
 -------
CCGGCCCT   846
```

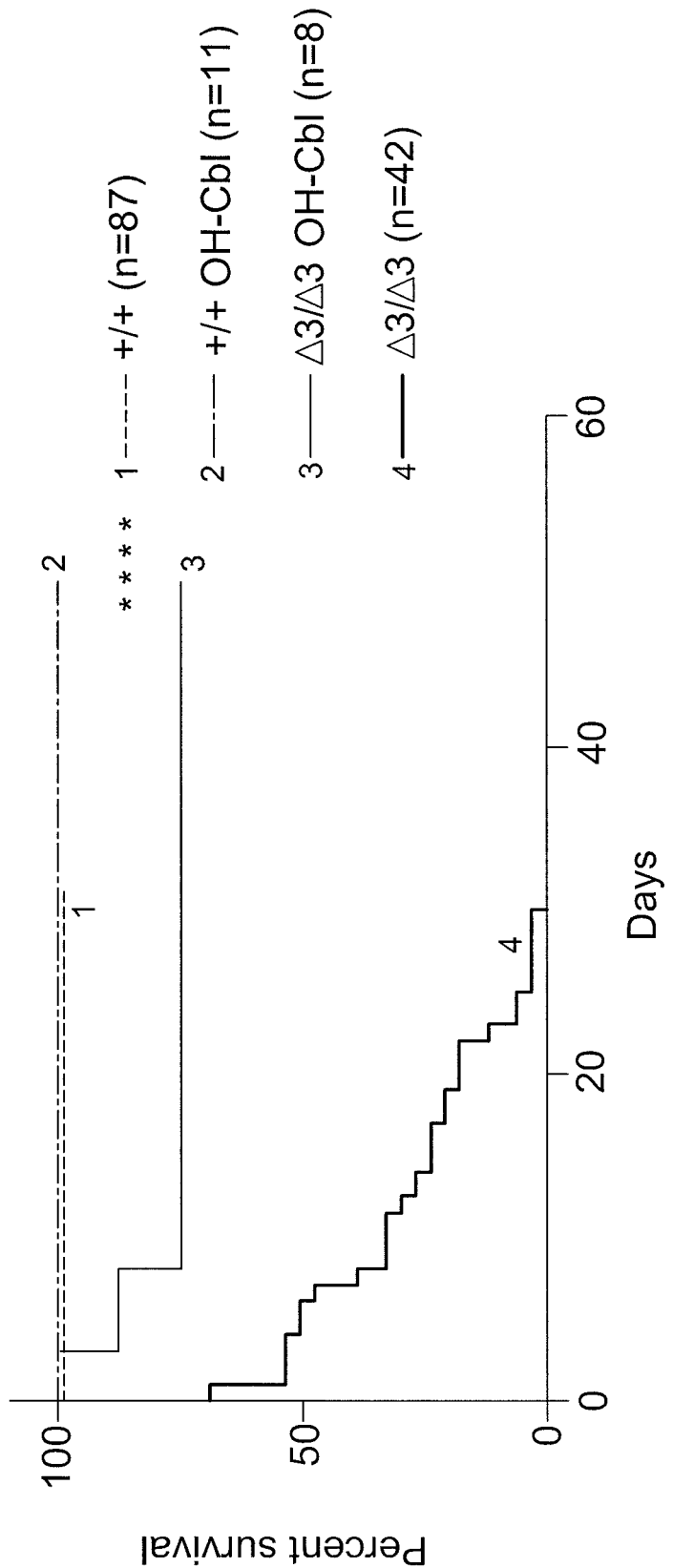

GENE THERAPY FOR COMBINED METHYLMALONIC ACIDEMIA/ACIDURIA AND HYPERHOMOCYSTEINEMIA/HOMOCYSTINURIA, COBALAMIN C TYPE, AND DEFICIENCY OF MMACHC

CROSS-REFERENCE TO RELATED APPLICATIONS

This patent application is a U.S. National Phase of International Patent Application No. PCT/ US2016/029512, filed Apr. 27, 2016, which claims the benefit of U.S. Provisional Patent Application No. 62/266,352, filed Dec. 11, 2015, and U.S. Provisional Patent Application No. 62/279,285, filed Jan. 15, 2016, each of which is incorporated herein by reference in its entirety.

STATEMENT REGARDING FEDERALLY SPONSORED RESEARCH AND DEVELOPMENT

This invention was made with Government support under project number Z01 HG-200318-11 by the National Institutes of Health, National Human Genome Research Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 47,704 Byte ASCII (Text) file named "739248_ST25.txt," dated Jun. 7, 2018.

BACKGROUND OF THE INVENTION

Patients with combined methylmalonic acidemia/aciduria and hyperhomocysteinemia/homocystinuria cobalamin C type (cobalamin C deficiency; cblC) are at risk for metabolic decompensation, thromboembolic events, manifest multisystemic disease and require lifelong daily intramuscular injections of cobalamin (vitamin B12) as well as treatment with other expensive medications such as carnitine, folinic acid, and betaine. Because they cannot synthesize adequate levels of methionine, the patients also require constant dietary and metabolic monitoring. Despite medical management, most children with cblC become legally blind by the age of 10 and have other neurological complications such as developmental delay, cognitive impairment, behavioral disorders, psychosis, thromboembolic stokes, and neuropathy.

There is a need for the development of more effective treatments of cblC, including those that are less burdensome to patients, especially those that treat the neurological and ocular manifestations of the disorder.

BRIEF SUMMARY OF THE INVENTION

In one embodiment, the present invention provides a synthetic methylmalonic acidemia cblC type with homocystinuria (MMACHC) polynucleotide comprising, consisting essentially of, or consisting of a polynucleotide encoding MMACHC that is codon-optimized for expression in a human. In another embodiment, the present invention provides a composition comprising, consisting essentially of, or consisting of a synthetic MMACHC polynucleotide and a pharmaceutically acceptable carrier.

In another embodiment, the present invention provides a polypeptide encoded by a synthetic MMACHC polynucleotide. In another embodiment, the present invention provides a composition comprising, consisting essentially of, or consisting of a MMACHC polypeptide and a pharmaceutically acceptable carrier.

In another embodiment, the present invention provides an expression vector comprising a MMACHC gene sequence under the control of a chicken beta actin (CBA) promoter. In another embodiment, the present invention provides an expression vector comprising a synthetic MMACHC polynucleotide. In another embodiment, the present invention provides a composition comprising, consisting essentially of, or consisting of an expression vector and a pharmaceutically acceptable carrier.

In another embodiment, the present invention provides a method of treating or preventing at least one condition of methylmalonic acidemia, hyperhomocysteinemia/homocystinuria, cobalamin C type and deficiency of MMACHC, and low levels of MMACHC in a subject, the method comprising, consisting essentially of, or consisting of administering to a subject in need thereof a therapeutically effective amount of (i) a synthetic MMACHC polynucleotide described herein; (ii) a composition described herein; (iii) a polypeptide described herein; or an expression vector described herein; wherein the administration treats the condition in the subject.

In another embodiment, the present invention provides a method for detecting or tracking exogenous MMACHC in a subject comprising, consisting essentially of, or consisting of: (a) administering to the subject exogenous MMACHC in the form of (i) a synthetic MMACHC polynucleotide described herein, or (ii) an expression vector described herein; (b) obtaining a sample of tissue, biospecimen, or body fluid from the subject; and (c) determining the expression level of the exogenous MMACHC in the sample.

BRIEF DESCRIPTION OF THE DRAWINGS

FIGS. 1A and 1B depict the BLASTN alignment between the wild-type MMACHC gene (top sequence; SEQ ID NO: 1) and the codon-optimized allele (bottom sequence; SEQ ID NO: 2). The genes have only 77% identity at the nucleotide level and widespread incomplete alignment. Score: 499 bits (270); Expect: 3e-145; Identities: 656/848 (77%); Gaps: 4/484 (0%); Strand: Plus/Plus.

FIG. 4A shows methylmalonic acid levels. FIG. 4B shows homocysteine levels. FIG. 4C shows methionine levels. $p<0.05$-$0.001$ for all metabolites.

FIG. 5 is a line graph showing hydroxocobalamin (OH-Cbl) treatment improves survival of Mmachc$^{\Delta 3/\Delta 3}$ mice (**** $p<0.001$, log-rank test, compared to $\Delta 3/\Delta 3$).

FIGS. 7A-7C are dot plots showing OH-Cbl improves biochemical phenotype in Mmachc$^{Δ3/Δ3}$ mice. FIG. 7A shows methylmalonic acid levels. FIG. 7B shows homocysteine levels. FIG. 7C shows methionine levels. *p<0.05, p<0.01, * p<0.001, "NS" is not significant.

FIG. 8A shows the codon-optimized (MMACHC cod. op.), MMACHC-HA (MMACHC cod. op.-HA) tagged and MMACHC-3×FLAG-tagged (MMACHC cod.op.-FLAG) protein levels compared to the wild-type mouse Mmachc after transfection of expression constructs into 293T cells and probing the cellular extracts with an anti-MMACHC antibody (AB1). An increased expression level of the codon-optimized alleles compared to the wild-type mouse gene can be easily appreciated. FIG. 8B shows the codon-optimized MMACHC and tagged alleles compared to the wild-type mouse Mmachc after transfection into 293T cells and probing with a second anti-MMACHC antibody (AB2). An increased expression level of the codon-optimized alleles compared to the wild-type mouse gene can be easily appreciated. FIG. 8C shows the codon-optimized MMACHC and tagged alleles compared to the wild-type mouse Mmachc after transfection into 293T cells and probing with an anti-HA antibody. A single allele containing the HA tag is recognized. FIG. 8D shows the codon-optimized and tagged MMACHC alleles compared to the wild-type mouse Mmachc after transfection into 293T cells and probing with an anti-FLAG antibody. A single allele containing the FLAG tag is recognized.

FIG. 9A shows an AAV vector with the wild-type human MMACHC. FIG. 9B shows an AAV vector with the wild-type mouse Mmachc. FIG. 9C shows an AAV vector with a codon-optimized, synthetic human MMACHC. FIG. 9D shows an AAV vector with a codon-optimized, synthetic human MMACHC tagged with hemagglutinin (HA). FIG. 9E shows an AAV vector with a codon-optimized, synthetic human MMACHC tagged with 3× FLAG.

DETAILED DESCRIPTION OF THE INVENTION

Figure 2:
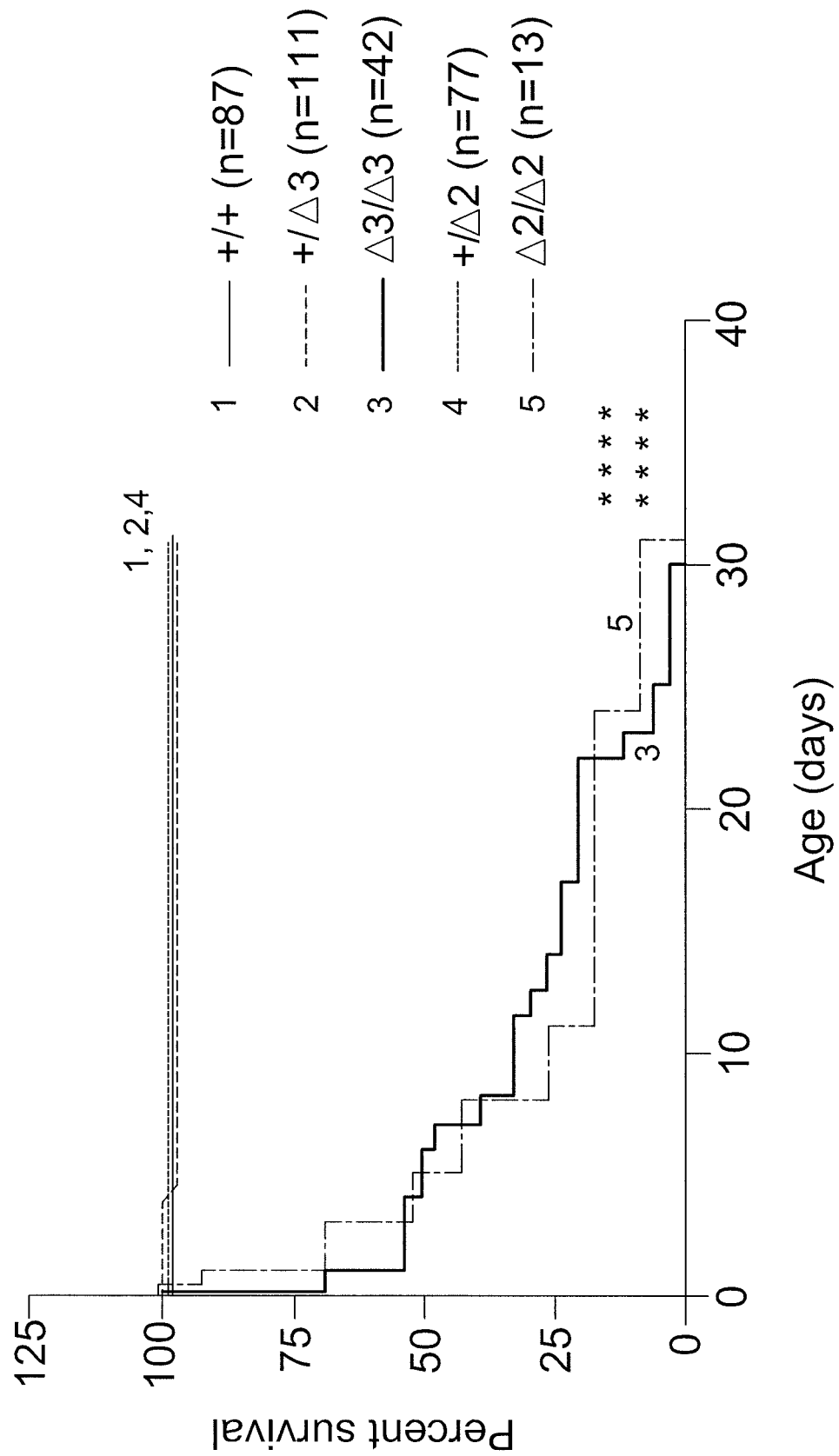
FIG. 2 is a line graph showing Mmachc$^{\Delta 3/\Delta 3}$ and Mmachc$^{\Delta 2/\Delta 2}$ mice exhibit reduced survival (****$p<0.0001$, compared to +/+).

Cobalamin C deficiency is the most common inborn error of intracellular cobalamin metabolism (Lerner-Ellis et al. Nat. Genet., 38: 93-100 (2006)) and is caused by mutations in MMACHC (GenBank NM_015506.2), a gene responsible for the processing and trafficking of intracellular cobalamin. Mutations in MMACHC impair the activity of two cobalamin-dependent enzymes: methylmalonyl-CoA mutase (MUT) and methionine synthase (MTR). Without wishing to be bound to any theory, MMACHC transports and processes intracellular cobalamin into its two active cofactors, 5'-adenosylcobalamin and methylcobalamin, necessary for the enzymatic reactions of MUT and MTR, respectively. Patients display methylmalonic acidemia, hyperhomocysteinemia, and hypomethionemia and variably manifest intrauterine growth retardation, anemia, heart defects, failure to thrive, white matter disease, neuropathy, neurocognitive impairment, and a progressive maculopathy, pigmentary retinopathy, and retinal degeneration that causes blindness, despite standard of care metabolic therapy (Carrillo-Carrasco et al., J. Inherit. Metab. Dis., 35: 103-14 (2012)).

Cobalamin deficiency type C (cblC) is often diagnosed based on newborn screening. While the true prevalence of the disorders of intracellular cobalamin metabolism is unknown, the historical incidence of cblC has been estimated at 1:200,000 births with about 400 cases reported in the literature; recently, data from newborn screening suggested a higher incidence closer to 1:100,000 in New York state and 1:60,000 in California, where an incidence of 1:37,000 was estimated in the Hispanic population. In one study of a Chinese population in Shangong province, it was claimed that 1:3920 births were affected (Han et al., Clinical presentation, gene analysis and outcomes in young patients with early-treated combined methylmalonic acidemia and homocysteinemia (cblC type) in Shandong province, China, Brain Dev., pii: S0387-7604(15)00228-4 (2015)).

Previous efforts to develop a viable animal model of cblC have proven unsuccessful. A knockout mouse generated from an Mmachc gene trap resulted in embryonic arrest by day E3.5 (Moreno-Garcia et al., Mol. Genet. Metab., 112: 198-204 (2014)). As shown in the Examples below, viable mouse models (Mmachc$^{Δ2/Δ2}$ and Mmachc$^{Δ3/Δ3}$) were developed and are described herein. The mouse models exhibit the phenotypic and biochemical features of patients with cblC. When treated using a conventional treatment (hydroxocobalamin), Mmachc$^{Δ3/Δ3}$ mice displayed improvement in disease characteristics, and Mmachc$^{Δ3/Δ3}$ mice have been used in developing treatments for patients with cblC, as described herein.

In one embodiment, the present invention provides a synthetic MMACHC polynucleotide comprising, consisting essentially of, or consisting of a polynucleotide encoding MMACHC that is codon-optimized for expression in a human. FIG. 1 shows a comparison of SEQ ID NO: 1 (wild-type MMACHC) with SEQ ID NO: 2 (codon-optimized MMACHC). In another embodiment, the polynucleotide encoding MMACHC comprises, consists essentially of, or consists of the sequence of SEQ ID NO: 2. In another embodiment, the polynucleotide encoding MMACHC has at least about 90% sequence homology with SEQ ID NO: 2. In another embodiment, the polynucleotide encoding MMACHC has at least about 95% sequence homology with SEQ ID NO: 2. The codon-optimized MMACHC gene or homologous gene can be associated with any suitable stop codon, for example the stop codon of TAA or TGA or together as two contiguous codons (TAATGA).

A polynucleotide is a nucleic acid. "Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, for the nucleic acid to comprise one or more insertions, deletions, inversions, and/or substitutions, such as with codon optimization.

The nucleic acids may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, which are well known in the art. The nucleic acids can be constructed based on chemical synthesis and/or enzymatic ligation reactions using procedures known in the art. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil -5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids can be purchased from companies.

Contemplated herein are any isolated or purified nucleotide sequence described herein. Alternatively, the nucleotide sequence can comprise a nucleotide sequence which is degenerate to any of the sequences or a combination of degenerate sequences or which is complementary to the nucleotide sequence of any of the nucleic acids described herein or a nucleotide sequence which hybridizes under stringent conditions to the nucleotide sequence of any of the nucleic acids described herein.

The nucleotide sequence that hybridizes under stringent conditions may hybridize under high stringency conditions.

By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions that would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand. It is generally appreciated that conditions can be rendered more stringent by the addition of increasing amounts of formamide.

The terms "complementary" and "complementarity" refer to the ability of a nucleic acid to form hydrogen bond(s) with another nucleic acid sequence by either traditional Watson-Crick base-paring or other non-traditional types of pairing. The degree of complementarity between two nucleic acid sequences, i.e., the homology, can be indicated by the percentage of nucleotides in a nucleic acid sequence which can form hydrogen bonds (e.g., Watson-Crick base pairing) with a second nucleic acid sequence (e.g., 50%, 60%, 70%, 80%, 90%, and 100% complementary). Two nucleic acid sequences are "perfectly complementary" if all the contiguous nucleotides of a nucleic acid sequence will hydrogen bond with the same number of contiguous nucleotides in a second nucleic acid sequence. Two nucleic acid sequences are "substantially complementary" if the degree of complementarity between the two nucleic acid sequences is at least 60% (e.g., 65%, 70%, 75%, 80%, 85%, 90%, 95%. 97%, 98%, 99%, or 100%) over a region of at least 8 nucleotides (e.g., 9, 10, 11, 12, 13, 14, 15, 16, 17, 18, 19, 20, 21, 22, 23, 24, 25, 30, 35, 40, 45, 50, or more nucleotides).

A codon-optimized polynucleotide is a polynucleotide, for example a naturally-occurring polynucleotide, that has been altered to improve expression in an organism, for example, a human or a cell line derived from a human.

In another embodiment, the polynucleotide further comprises a tag, wherein the tag can be an epitope tag. In another embodiment, the polynucleotide further comprises a polynucleotide encoding at least one of a hemagglutinin tag and a 3×FLAG tag. A tag facilitates detection, and epitope tags are protein regions that can be identified using immunoassay techniques. For example, an epitope tag can be recognized by an antibody or a binding portion thereof (e.g., scFv). In another embodiment, the polynucleotide encoding the hemagglutinin tag comprises, consists essentially of, or consists of the sequence of SEQ ID NO: 3. In another embodiment, the polynucleotide encoding the hemagglutinin tag has at least about 90% sequence homology with SEQ ID NO: 3. In another embodiment, the polynucleotide encoding the hemagglutinin tag has at least about 95% sequence homology with SEQ ID NO: 3. In another embodiment, the polynucleotide encoding the 3×FLAG tag comprises, consists essentially of, or consists of the sequence of SEQ ID NO: 4. In another embodiment, the polynucleotide encoding the 3×FLAG tag has at least about 90% sequence homology with SEQ ID NO: 4. In another embodiment, the polynucleotide encoding the 3×FLAG tag has at least about 95% sequence homology with SEQ ID NO: 4. In yet another embodiment, the tag can include others recognized by practitioners of the art, including His, c-myc, GST, Protein A, CD, Strep-tag, MBP, CBD, S-tag, Avitag, CBP, TAP, SF-TAP or others that would allow facile detection, purification, assay and biodistribution of the tag affixed to a codon-optimized MMACHC protein or nucleic acid.

In another embodiment, the present invention provides a polypeptide encoded by a synthetic MMACHC polynucleotide. The polypeptide can be altered so long as the polypeptide has substantially the same activity as wild-type MMACHC and can include a functional portion of MMACHC. The term "functional portion" refers to any part or fragment of MMACHC, which part or fragment retains the biological activity of MMACHC. Functional portions encompass, for example, those parts of MMACHC that retain the ability of processing and trafficking intracellular cobalamin. In reference to MMACHC, the functional portion can comprise, for instance, about 10%, 25%, 30%, 50%, 68%, 80%, 90%, 95%, or more, of MMACHC.

The functional portion can comprise additional amino acids at the amino or carboxy terminus of the portion, or at both termini, which additional amino acids are not found in the amino acid sequence of MMACHC. Desirably, the additional amino acids do not interfere with the biological function of the functional portion. More desirably, the additional amino acids enhance the biological activity, as compared to the biological activity of MMACHC.

Contemplated herein are functional variants of MMACHC. The term "functional variant" as used herein refers to a polypeptide or protein having substantial or significant sequence identity or similarity to MMACHC, which functional variant substantially retains the biological activity of MMACHC. Functional variants encompass, for example, those variants of MMACHC that retain the ability of processing and trafficking intracellular cobalamin to a similar extent, the same extent, or to a higher extent, as MMACHC. In reference to MMACHC, the functional variant can, for instance, be at least about 30%, 50%, 75%, 80%, 90%, 98% or more identical in amino acid sequence to MMACHC.

A functional variant can, for example, comprise the amino acid sequence of MMACHC with at least one conservative amino acid substitution. Alternatively or additionally, the functional variants can comprise the amino acid sequence of MMACHC with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to MMACHC.

Amino acid substitutions are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The MMACHC polypeptide can consist essentially of the specified amino acid sequence or sequences described herein, such that other components e.g., other amino acids, do not materially change the biological activity of the functional variant.

The MMACHC polypeptide (including functional portions and functional variants) can be of any length, i.e., can comprise any number of amino acids, provided that the MMACHC (or functional portions or functional variants thereof) retain their biological activity, e.g., of processing and trafficking intracellular cobalamin. For example, the polypeptide can be about 50 to about 5000 amino acids long, such as 50, 70, 75, 100, 125, 150, 175, 200, 300, 400, 500, 600, 700, 800, 900, 1000 or more amino acids in length. In this regard, the polypeptides also include oligopeptides.

The MMACHC polypeptide (including functional portions and functional variants) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The MMACHC polypeptide (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The MMACHC polypeptide (including functional portions and functional variants thereof) can be obtained by methods known in the art. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, $3^{rd}$ ed., Cold Spring Harbor Press, Cold Spring Harbor, N.Y. 2001; and Ausubel et al., Current Protocols in Molecular Biology, Greene Publishing Associates and John Wiley & Sons, N Y, 1994.

Further, MMACHC (including functional portions and functional variants thereof) can be isolated and/or purified from a source, such as a plant, a bacterium, an insect, a mammal, e.g., a rat, a human, etc. Methods of isolation and purification are well-known in the art. Alternatively, the MMACHC (including functional portions and functional variants thereof) can be commercially synthesized by companies. In this respect, the MMACHC can be synthetic, recombinant, isolated, and/or purified.

The term "isolated" as used herein means having been removed from its natural environment. The term "purified" or "isolated" does not require absolute purity or isolation; rather, it is intended as a relative term. Thus, for example, a purified (or isolated) protein preparation is one in which the protein is more pure than the protein in its natural environment within a cell. Such proteins may be produced, for example, by standard purification techniques, or by recombinant expression. In some embodiments, a preparation of a protein is purified such that the protein represents at least about 50%, for example at least about 70%, of the total protein content of the preparation. For example, the purity can be at least about 50%, can be greater than about 60%, about 70% or about 80%, or can be about 100%.

An embodiment provides recombinant expression vectors comprising any of the nucleic acids described herein. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host. Suitable vectors include those designed for propagation and expansion or for expression or both, such as plasmids and viruses. The vector can be selected from bacterial expression systems such as PET or one that can direct expression in yeast such as pYES or even used to make a mammalian cell line for overproduction of MMACHC in such cells as Chinese hamster ovary or others know to practitioners of the art.

In another embodiment, the codon-optimized MMACHC gene and tagged alleles can be used, in combination with genome editing and homologous recombination, to create cell lines that over express MMACHC and/or tagged alleles from a specific endogenous genomic location, such as in the albumin gene, or from a safe-harbor. Inducible and regulatable control of the recombinant MMACHC alleles is also envisioned.

The terms "transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)).

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ SV40, bovine papilloma virus, and the like.

The recombinant expression vector may comprise regulatory sequences, such as transcription and translation initiation and termination codons, which are specific to the type of host (e.g., bacterium, fungus, plant, or animal) or tissue into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide protrophy, and the like. Suitable marker genes include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the MMACHC nucleotide sequence (including functional portions and functional variants thereof), or to the nucleotide sequence which is complementary to or which hybridizes to the nucleotide sequence encoding MMACHC. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-teiniinal repeat of the murine stem cell virus. In another embodiment, the present invention provides an expression vector comprising a MMACHC gene sequence under the control of a chicken beta actin (CBA) promoter. In another embodiment, the present invention provides an expression vector comprising a synthetic MMACHC polynucleotide. In another embodiment, the synthetic MMACHC polynucleotide is under the control of a chicken beta actin (CBA) promoter.

In addition to the nucleic acid sequence encoding the MMACHC, the vector preferably comprises expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990). The recombinant expression vectors can be designed for either transient expression, for stable expression, or for both. Also, the recombinant expression vectors can be made for constitutive expression or for inducible expression.

The recombinant expression vector may be a viral vector, e.g., a retroviral vector. In another embodiment, the expression vector is a viral vector. In another embodiment, the vector is an adenovirus, or a helper-dependent adenovirus. In another embodiment, the vector is a herpes viral vector. In yet another embodiment, the vector is an integrating vector, such as a lentiviral vector.

In another embodiment, the viral vector is a single-stranded adeno-associated viral (AAV) vector. The AAVs can be derived from serotypes well-known to practitioners of the art, including AAV 1, 2, 3, 4, 5, 6, 8, 9, rh8, rh10, rh33, and rh34. Chimeras between these serotypes and point mutations of said serotypes are contemplated, such as tyrosine mutants of serotypes 2, 5, 6, 8 and 9, as are mutants in surface exposed tyrosine (Y) and threonine (T) residues on the capsids (Bogner et al., PLoS One, 10(6):e0128759 (2015); Kay et al., PLoS One, 8(4):e62097 (2013), erratum in: PLoS One, 8(9) (2013); Qiao et al., Hum. Gene Ther. Methods, 23(1):29-37 (2012); Ryalsv et al., Mol Vis., 17:1090-102 (2011); Markusic et al., Mol. Ther., 18(12): 2048-56 (2010); Qiao et al., Hum. Gene Ther., 21(10): 1343-8 (2010); Petrs-Silva et al., Mol. Ther., 17(3):463-71 (2009); each of which are individually incorporated by reference herein in its entirety). Also considered are capsids derived by in vitro evolution and selection, such as 7m8 (Dalkara et al., Sci. Transl. Med., 5(189):189ra76 (2013), incorporated by reference herein in its entirety) and those derived by phylogenetic reconstruction such as Anc80 and relatives (Santiago-Ortiz et al., Gene Ther., 22(12):934-46 (2015), incorporated by reference herein in its entirety). The vector can be, for example, Anc80 and others as described in Zinn et al., Cell Rep., 12(6):1056-1068 (2015), incorporated by reference herein in its entirety.

In another embodiment, the viral vector is constructed in the self-complimentary (sc) configuration as is well known to practitioners of the art. scAAVs designed to express the codon-optimized MMACHC gene or tagged alleles may have increased potency and can be encapsidated with any of the aforementioned serotypes.

The AAVs expressing MMACHC and variants can be purified after transfection methods using 293 cells of an equivalent, produced in insect cells or using herpes-based systems. Such methods are well known to practitioners of the art.

Using an AAV expressing MMACHC or one configured to correct an MMACHC patient cell line, hematopoietic stem and progenitor cells can be transduced with an AAV6 donor and homologous recombination can be used to correct the mutant allele using genome editing (Wang et al., Nat. Biotechnol., 33(12):1256-1263 (2015), incorporated by reference herein in its entirety). This can be accomplished with mRNA expressing ZFNs, TALENS or the CAS-CRISPR system. The corrected or transduced MMACHC cells can then be used as a source of cellular therapy.

In another embodiment, an AAV vector can be designed to enable promoterless correction, either at a safe harbor location in the genome or into predetermined cellular target gene, ex vivo or in vivo (Barzel et al., Nature, 517(7534): 360-364 (2015), incorporated by reference herein in its entirety).

The AAV may be selected such that there is improvement of infection of a target tissue. In another embodiment, the AAV is pseudotyped with at least one of rh10, type 9, or type 8 capsid. Further examples include the AAVs of U.S. Patent Publication No. 2014/0364338, incorporated by reference herein in its entirety, which have altered capsid proteins for greater infectivity of retinal cells.

In another embodiment, the present invention provides an expression vector comprising, consisting essentially of, or consisting of any one of SEQ ID NOS: 5-9. In another embodiment, the present invention provides an expression vector comprising, consisting essentially of, or consisting of at least about 90% sequence homology with any one of SEQ ID NOS: 5-9. In another embodiment, the present invention provides an expression vector comprising, consisting essentially of, or consisting of at least about 95% sequence homology with any one of SEQ ID NOS: 5-9.

In another embodiment, the present invention provides a method of treating or preventing at least one condition of methylmalonic acidemia, homocystinuria, cobalamin C type and deficiency of MMACHC, and low levels of MMACHC in a subject, the method comprising, consisting essentially of, or consisting of administering to a subject in need thereof a therapeutically effective amount of (i) a synthetic MMACHC polynucleotide described herein; (ii) a composition described herein; (iii) a polypeptide described herein; or an expression vector described herein; wherein the administration treats the condition in the subject.

In another embodiment, the present invention provides a method of treating or preventing a disorder associated with MMACHC deficiency such as congenital heart defects (CHD), neural tube defects (NTD), combined methylmalonic acidemia and homocystinuria X type (cblX), HCFC1 spectrum defects, hyperhomocystinuria, and vitamin B12 deficiency (including recalcitrant vitamin B12 deficiency) in a subject, the method comprising, consisting essentially of, or consisting of administering to a subject in need thereof a therapeutically effective amount of (i) a synthetic MMACHC polynucleotide described herein; (ii) a composition described herein; (iii) a polypeptide described herein; or an expression vector described herein; wherein the administration treats the condition in the subject. As an example, patients with cblX deficiency caused by HCFC1 mutations are also deficient in the expression of MMACHC and suffer from combined methylmalonic acidemia and hyperhomocystinemia (Yu et al., Am. J. Hum. Gen., 93: 506-514 (2013), incorporated by reference herein in its entirety) and would benefit from increased MMACHC.

In another embodiment, the subject has vision loss and the administration is to the eye(s) of the subject. Most patients with cblC develop a bulls' eye maculopathy during infancy despite early identification by newborn screening and treatment with hydroxocobalamin and other cofactors. In early childhood, retinal degeneration progresses and optic nerve atrophy develops resulting in progressive vision loss until most children are legally blind by the end of the first decade of life. Prior to the present invention, there was no treatment for the eye disease of cobalamin C deficiency or deficiency of MMACHC, or the vision loss that accompanies it. A specific form of AAV mediated ocular gene therapy is envisioned using the invention described herein. The AAV can be delivered by subretinal injection, intravitreal injection, and/or retinal artery or vein injection.

In another embodiment, the present invention provides a method for detecting or tracking exogenous MMACHC in a subject comprising, consisting essentially of, or consisting of: (a) administering to the subject exogenous MMACHC in the form of (i) a synthetic MMACHC polynucleotide described herein, or (ii) an expression vector described herein; (b) obtaining a sample of tissue, biospecimen, or body fluid from the subject; and (c) determining the expression level of the exogenous MMACHC in the sample. Determining the expression level can be achieved by, for example, detecting or tracking RNA or protein levels of MMACHC. Detecting or tracking protein levels can involve, for example, detecting an expression tag associated with the MMACHC (e.g., using Western blot techniques), as described herein.

Further, the activity of MMACHC and its distribution can be detected or tracked using nucleic acid probes and nucleic acid detection methods. Because the codon-optimized MMACHC and tagged alleles share only 77% or less identity with wild-type at the nucleotide level, a facile detection using nucleic acid methods is envisioned. This includes qPCR, droplet PCR, RT-PCR as well as hybridization and polymerase amplification methods. In another embodiment, mass spectrometry and MALDI-TOF methods can be used to detect the codon-optimized nucleic acid in solution, tissues samples, biospecimens, and body fluids.

A biospecimen may include any tissue or cells, including white and red blood cells, saliva and salivary DNA, cell shed in the urine or feces, or any other organ that requires more invasive assessment by biopsy, such as liver, eye, retina, kidney, bone or skeletal muscle. A body fluid might include urine, plasma, serum, cerebrospinal fluid, aqueous humor, or feces.

In another embodiment, the present invention provides a composition comprising, consisting essentially of, or consisting of a synthetic MMACHC polynucleotide and a pharmaceutically acceptable carrier. In another embodiment, the present invention provides a composition comprising, consisting essentially of, or consisting of a MMACHC polypeptide and a pharmaceutically acceptable carrier. In another embodiment, the present invention provides a composition comprising, consisting essentially of, or consisting of an expression vector and a pharmaceutically acceptable carrier.

In certain embodiments, pharmaceutical composition are contemplated, comprising any of the nucleic acids, polypeptides, proteins, functional portions, functional variants, and expression vectors described herein and a pharmaceutically acceptable carrier. The pharmaceutical compositions can comprise more than one material, e.g., a polypeptide and a nucleic acid. Alternatively, the pharmaceutical composition can comprise a combination with other pharmaceutically active agents or drugs.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

Methods for preparing administrable (e.g., parenterally administrable) compositions are known or apparent to those skilled in the art and are described in more detail in, for example, Remington: The Science and Practice of Pharmacy, Lippincott Williams & Wilkins; 21st ed. (May 1, 2005).

The following formulations for oral, aerosol, parenteral (e.g., subcutaneous, intravenous, portal, intraarterial, intramuscular, intradermal, interperitoneal, and intrathecal), and rectal, and vaginal administration are merely exemplary and are in no way limiting. More than one route can be used for administration, and in certain instances, a particular route can provide a more immediate and more effective response than another route. The delivery of codon-optimized MMACHC via subretinal, intravitreal, transcranial, or epidural routes can also be used.

Formulations suitable for oral administration can comprise or consist of (a) liquid solutions, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can include a flavor, usually sucrose and acacia or tragacanth, as well as pastilles comprising the material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration can be in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a phannaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are contemplated. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Topical formulations, including those that are useful for transdermal drug release, are well known to those of skill in the art and are suitable for application to skin.

The gene and alleles can also be formulated as nucleic acids and encapsulated into lipid nanoparticles, or prepared as peptide nucleic acids and delivered in this fashion.

An "effective amount" or "an amount effective to treat" or "therapeutically effective amount" refers to a dose that is adequate to prevent or treat cobalamin C disease or MMACHC deficiency in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. For example, the dosing may range from a single systemic AAV injection at a dose of $2.5 \times 10^9$ genome copies/kilogram to a higher dose, on the order of $1 \times 10^{10-12}$ genome copies per eye, delivered by intravitreous or subretinal injection.

Additionally, the use of MMACHC, as a treatment for other forms of hyperhomocysteinemia, is encompassed herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cblC in a mammal. Furthermore, the treatment or prevention provided by the inventive method can include treatment or prevention of one or more conditions or symptoms of cblC being treated or prevented. Also, for purposes herein, "prevention" can encompass delaying the onset of the disease, or a symptom or condition thereof.

The subject can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

The following examples further illustrate the invention but, of course, should not be construed as in any way limiting its scope.

EXAMPLE 1

This example demonstrates the development of mouse models of human cblC.

To create a viable animal model of cblC deficiency, TALEN-mediated genome editing (Transposagen Biopharmaceuticals, Lexington, Ky., USA) was used to edit exon 2 of Mmachc in mice, near the location of the common mutation seen in humans—c.271dupA p.R91KfsX14. This technique is known to practitioners of the art (Qiu et al., Nucleic Acids Res., 41:e120 (2013), incorporated by reference herein in its entirety). Eleven founder mice harboring 10 different alleles were generated. Two mutations were further investigated: an early frameshift null allele [cDNA mutation c.165_166delAC giving protein mutation p.P56CfsX4 (Δ2)] and another [cDNA mutation c.162_164delCAC giving protein mutation p.S54_T55delinsR (Δ3)] that results in a deletion-insertion predicted to produce an intact but mutant enzyme. Founder mice harboring mutant alleles were bred to make stable transmitting lines, which were then intercrossed to produce homozygote affected animals with Mmachc deficiency.

At birth, an expected 1:2:1 Mendelian segregation was observed for the Mmachc$^{\Delta 3}$ allele (n=30 litters, 218 mice, $\chi^2$ p>0.1) but not for Mmachc$^{\Delta 2}$ (n=19 litters, 134 mice, $\chi^2$ p<0.001), in which the proportion of Mmachc$^{\Delta 2/\Delta 2}$ mice was decreased, suggesting partial embryonic lethality caused by this mutation (Table 1).

TABLE 1

| Mmachc parental genotype | | Offspring Mmachc genotype distribution | | | Number of litters | $\chi^2$ | df | p-value |
|---|---|---|---|---|---|---|---|---|
| Dam | Sire | +/+ | +/− | −/− | | | | |
| +/Δ3 | +/Δ3 | 54 | 120 | 44 | 30 (n = 218) | 3.13 | 2 | p > 0.1 |
| +/Δ2 | +/Δ2 | 39 | 81 | 14 | 19 (n = 134) | 15.18 | 2 | p < 0.001 |

All mice have FVB/N C57/B6 mixed background

Figure 3:
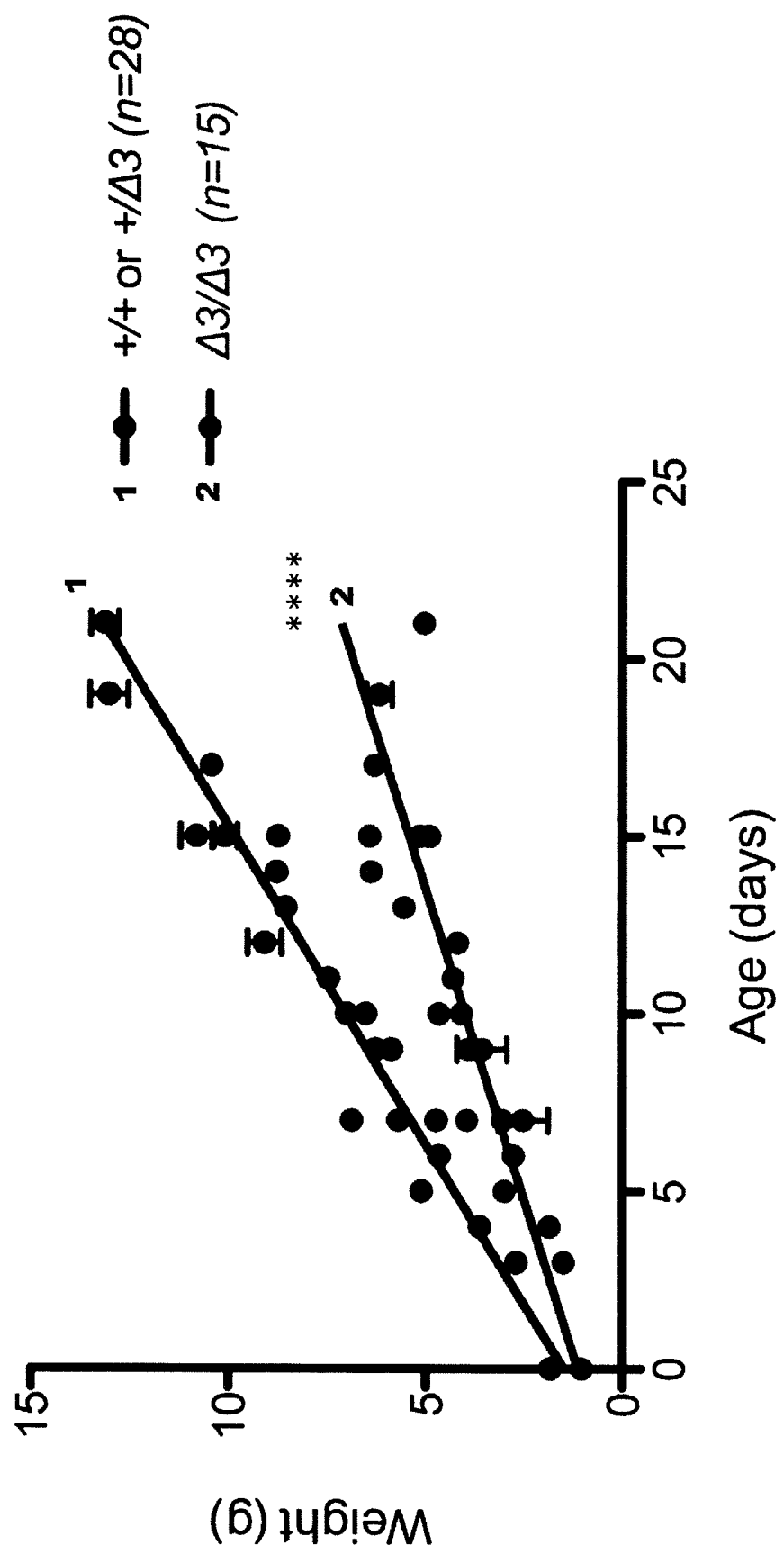
FIG. 3 is a line graph showing Mmachc$^{\Delta 3/\Delta 3}$ mice exhibit reduced growth. Weight is average weight of pup(s) of the Mmachc$^{\Delta 3/\Delta 3}$ genotype from a given litter compared to heterozygotes and wild-type controls from the same litters on a given day (**** $p<0.0001$).

Mmachc$^{\Delta 2/\Delta 2}$ and Mmachc$^{\Delta 3/\Delta 3}$ mice were growth retarded and displayed decreased survival with 100% lethality by 32 days (FIGS. 2 and 3). Survival of heterozygote mice does not differ significantly from wild-type mice for either allele. The survival curves for Mmachc$^{\Delta 3/\Delta 3}$ and Mmachc$^{\Delta 2/\Delta 2}$ mice do not differ significantly.

Figure 4A:
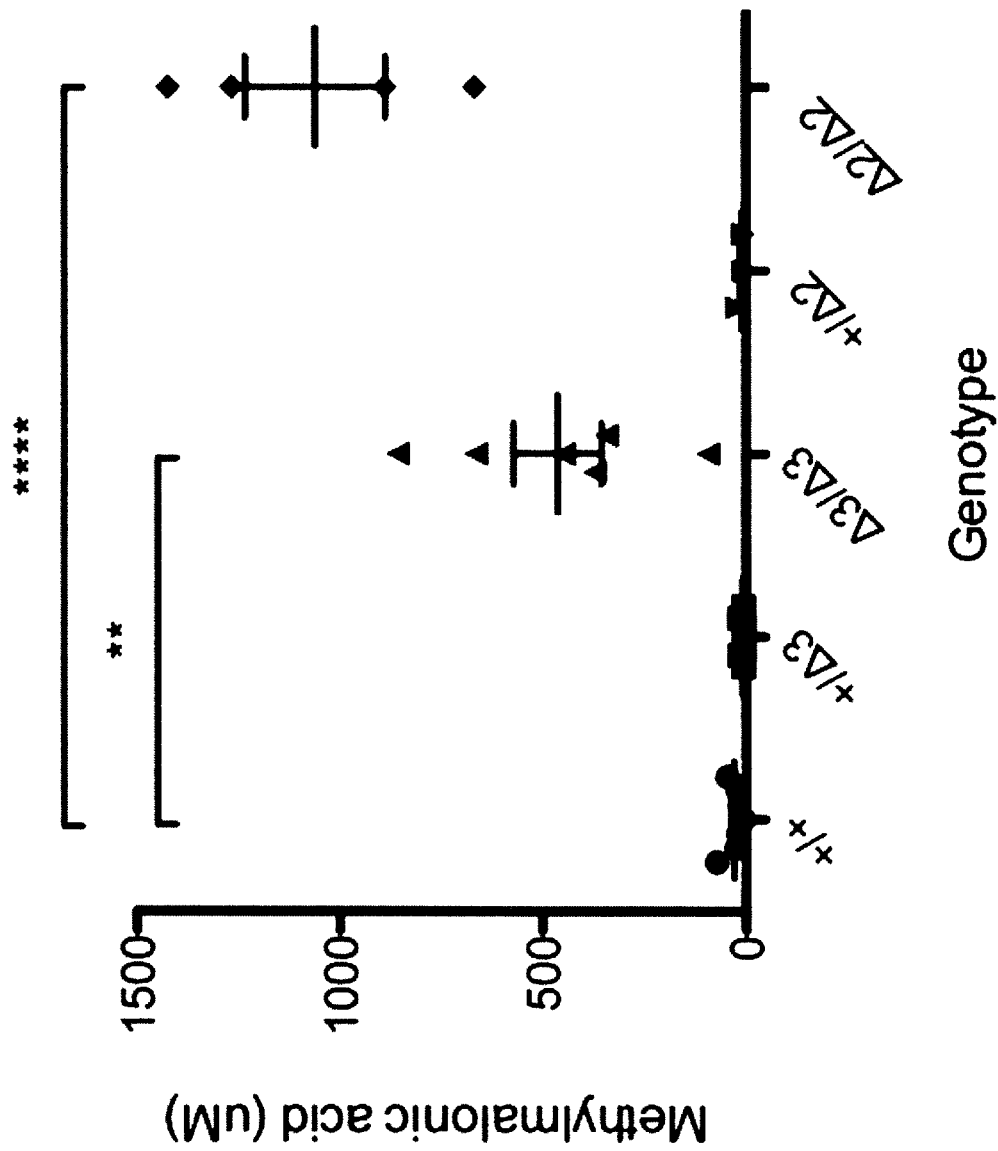
FIGS. 4A-4C are dot plots showing Mmachc$^{\Delta 3/\Delta 3}$ mice display a characteristic biochemical phenotype of cblC.
Figure 4B:
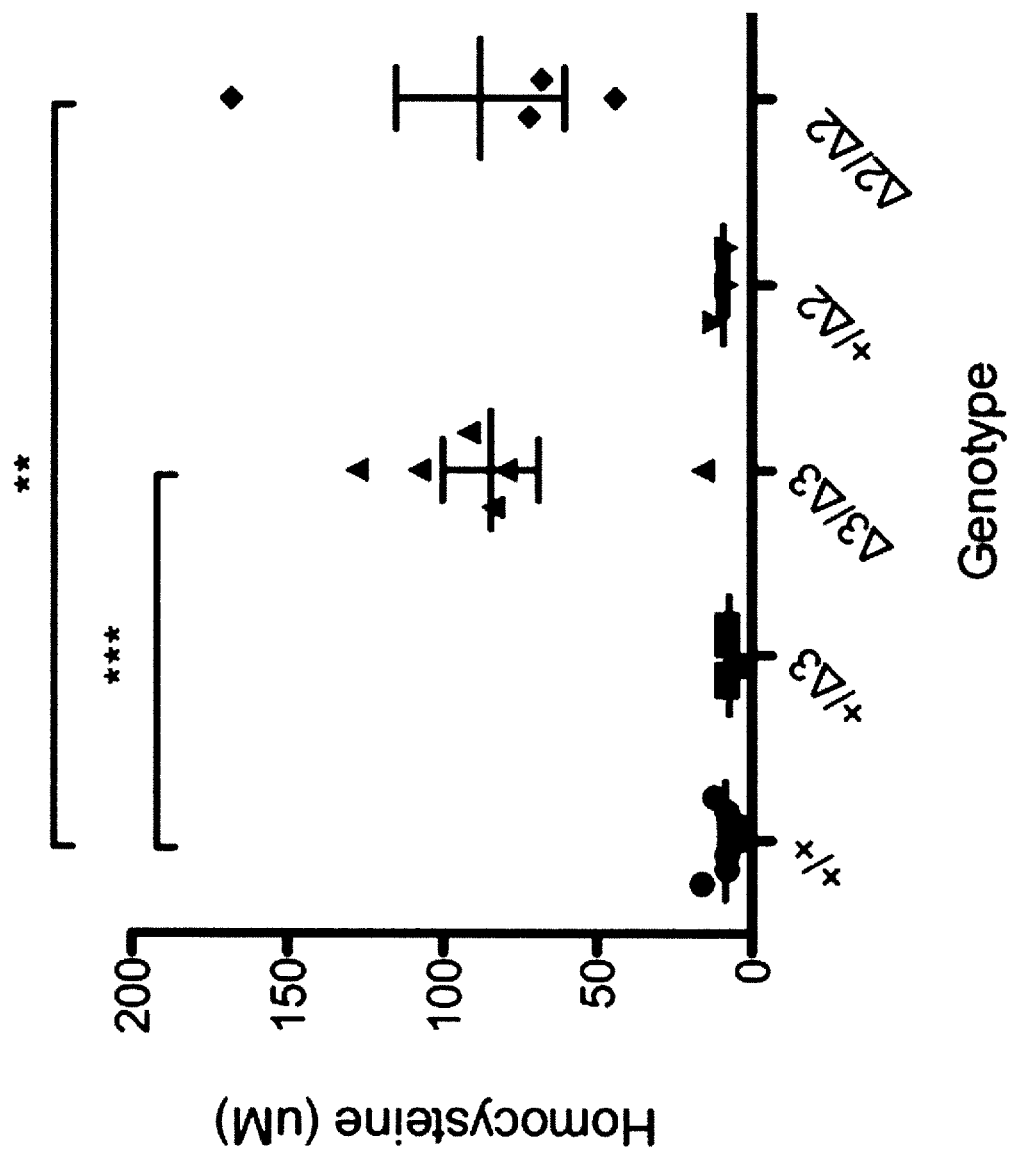
Figure 4C:
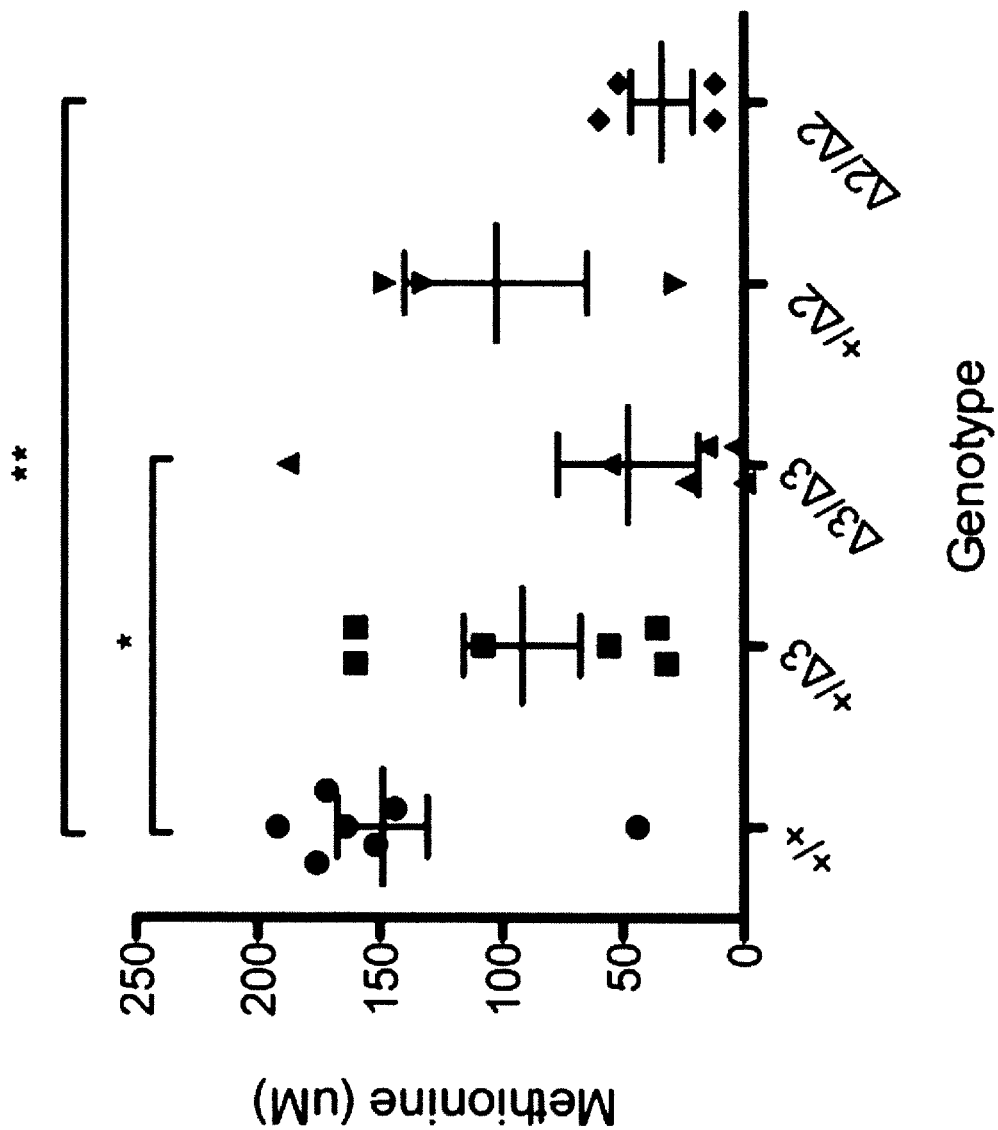

Compared with wild-type controls (n=7), Mmachc$^{\Delta 2/\Delta 2}$ (n=4) and Mmachc$^{\Delta 3/\Delta 3}$ (n=6) mutants displayed significantly elevated plasma methylmalonic acid (FIG. 4A), homocysteine (FIG. 4B), and decreased methionine (FIG. 4C). Also, Mmachc$^{\Delta 3/\Delta 3}$ mice display hepatic lipidosis and eye pathology similar to human cblC, including thinner outer nuclear layer with fewer nuclei and reduction in photoreceptor outer segments.

These mouse models represent viable mammalian models of cblC deficiency and recapitulate the phenotypic and biochemical features of the human disorder. The models presented with cblC-related biochemical perturbations (methylmalonic acidemia, hyperhomocysteinemia, and hypomethioninemia), exactly as present in the human patient population. In addition, both mutants showed hypopigmentation.

EXAMPLE 2

This example demonstrates treatment of cblC in Mmachc$^{\Delta 3/\Delta 3}$ mice using hydroxocobalamin (OH-Cbl).

Mice received prenatal treatment via maternal injections of 25-50 μg two times per week and postnatal treatment via injection of the same dose of 25-50 μg two to three times per week.

Mmachc$^{\Delta 3/\Delta 3}$ mice treated with OH-Cbl display significantly increased survival compared to non-treated Mmachc$^{\Delta 3/\Delta 3}$ mice (FIG. 5). Survival of Mmachc$^{\Delta 3/\Delta 3}$ mice treated with OH-Cbl does not differ significantly from treated Mmachc mice.

Figure 6:
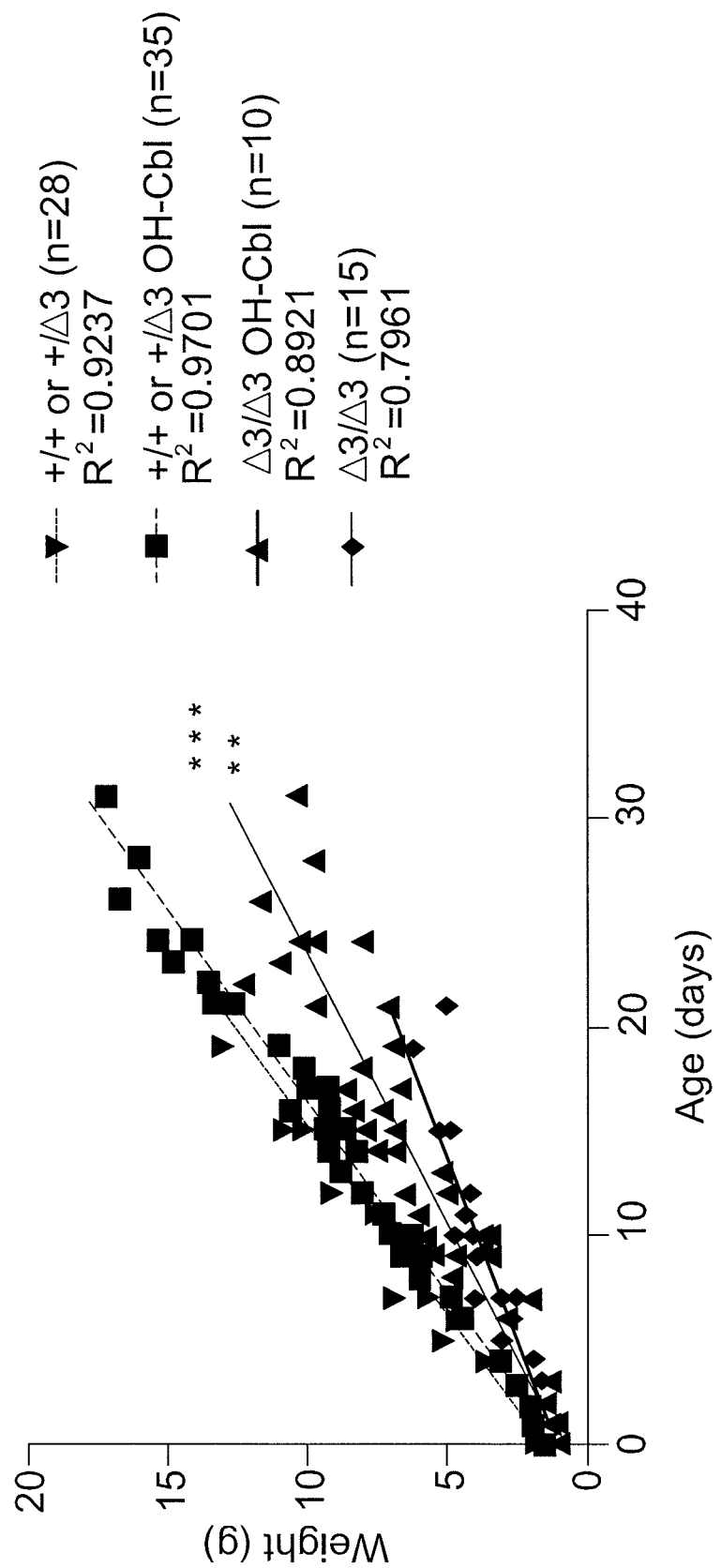
FIG. 6 is a line graph showing OH-Cbl treatment improves growth of Mmachc$^{\Delta 3/\Delta 3}$ mice, compared with Δ3/Δ3 (* p<0.001) compared with untreated Mmachc$^{Δ3/Δ3}$ mice ( p<0.005) but does not normalize (*** p<0.001) compared to controls.

Mmachc$^{\Delta 3/\Delta 3}$ mice treated with OH-Cbl display increased growth compared to non-treated Mmachc$^{\Delta 3/\Delta 3}$ mice (FIG. 6).

Figure 7A:
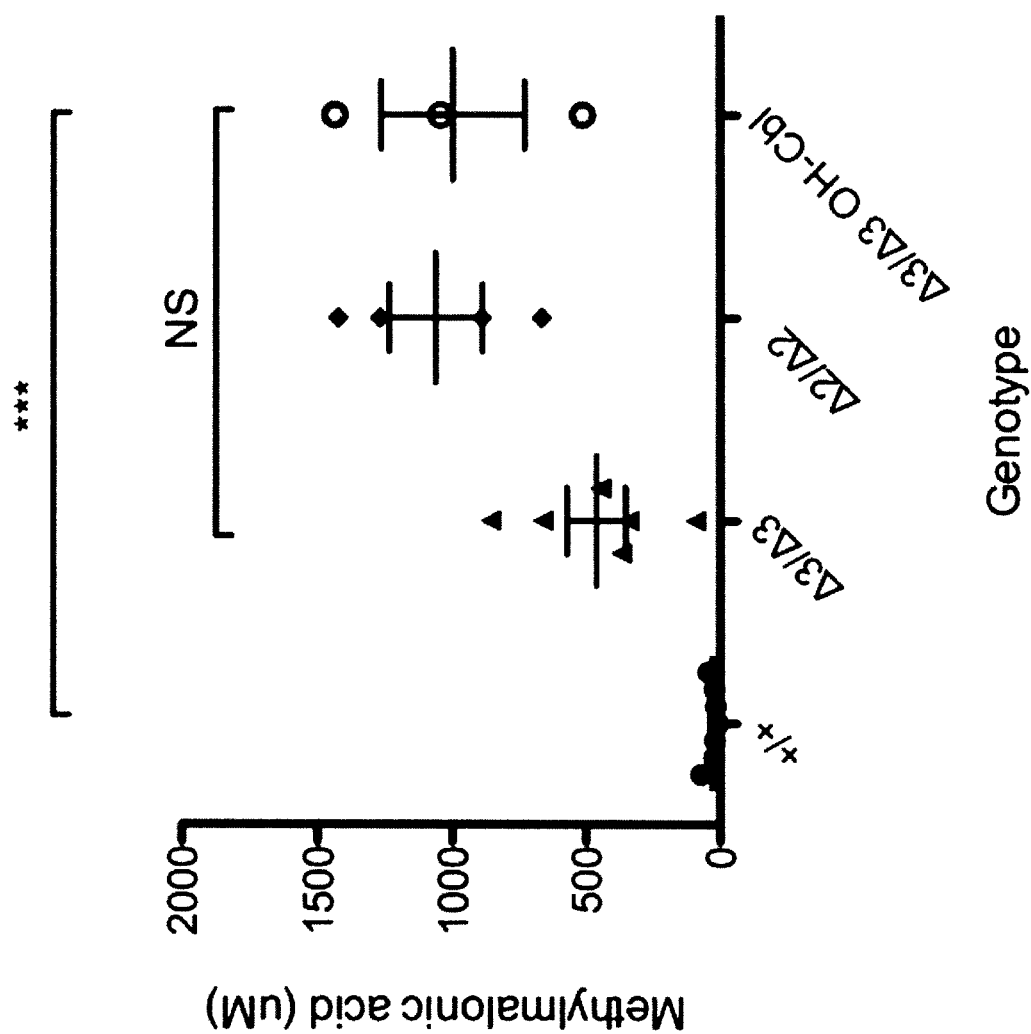
Figure 7B:
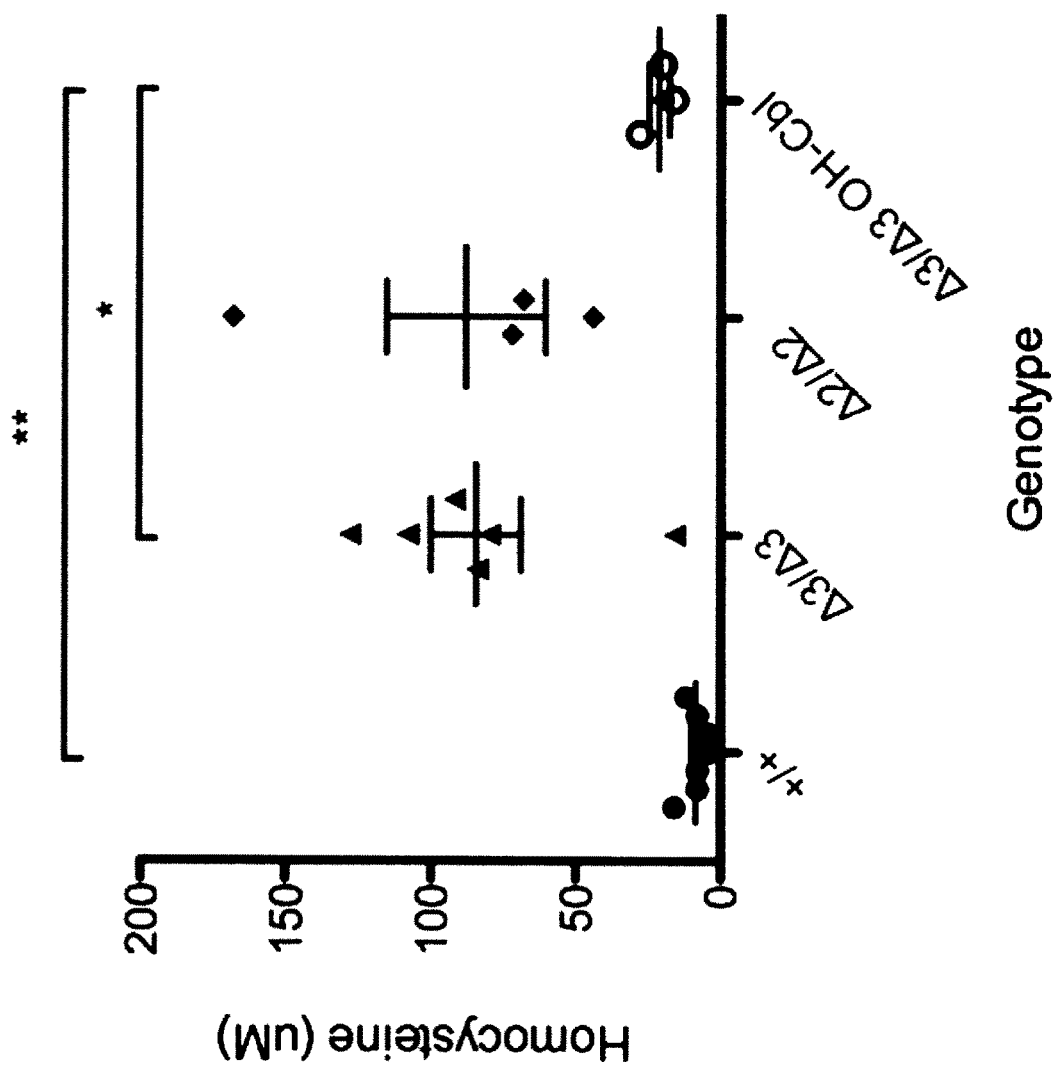

Mmachc$^{\Delta 3/\Delta 3}$ mice treated with OH-Cbl also display improvement in biochemical phenotype (FIGS. 7A-7C). Methylmalonic acid and methionine were found to be more dependent on diet, where a larger sample size is needed.

Also, it was found that OH-Cbl treatment reverses hypopigmentation in Mmachc$^{\Delta 3/\Delta 3}$ mice.

EXAMPLE 3

This example demonstrates the development of improved expression of MMACHC by codon optimization.

Figure 8:
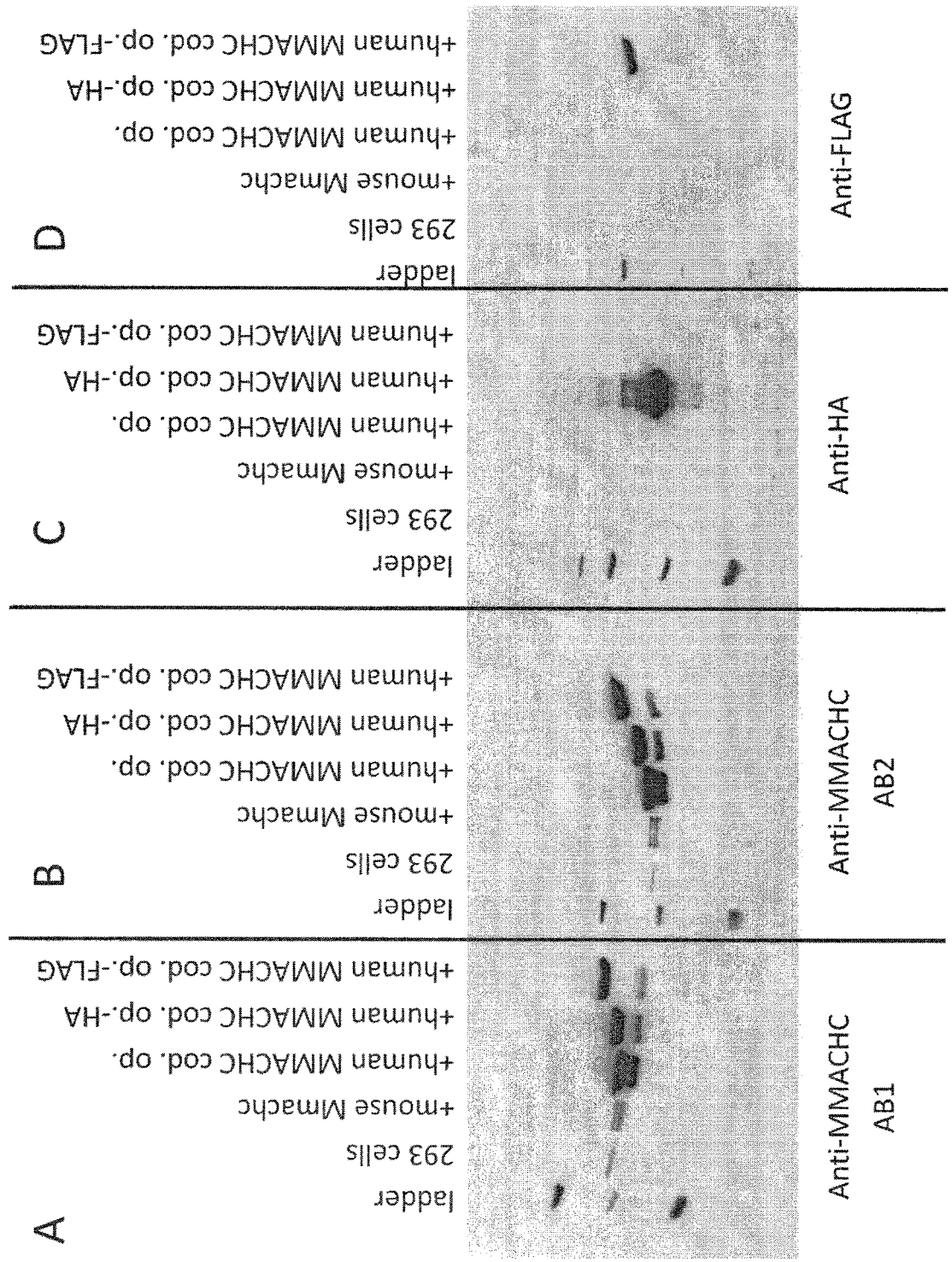
FIGS. 8A-8D show the expression of various MMACHC constructs.
Figure 9A:
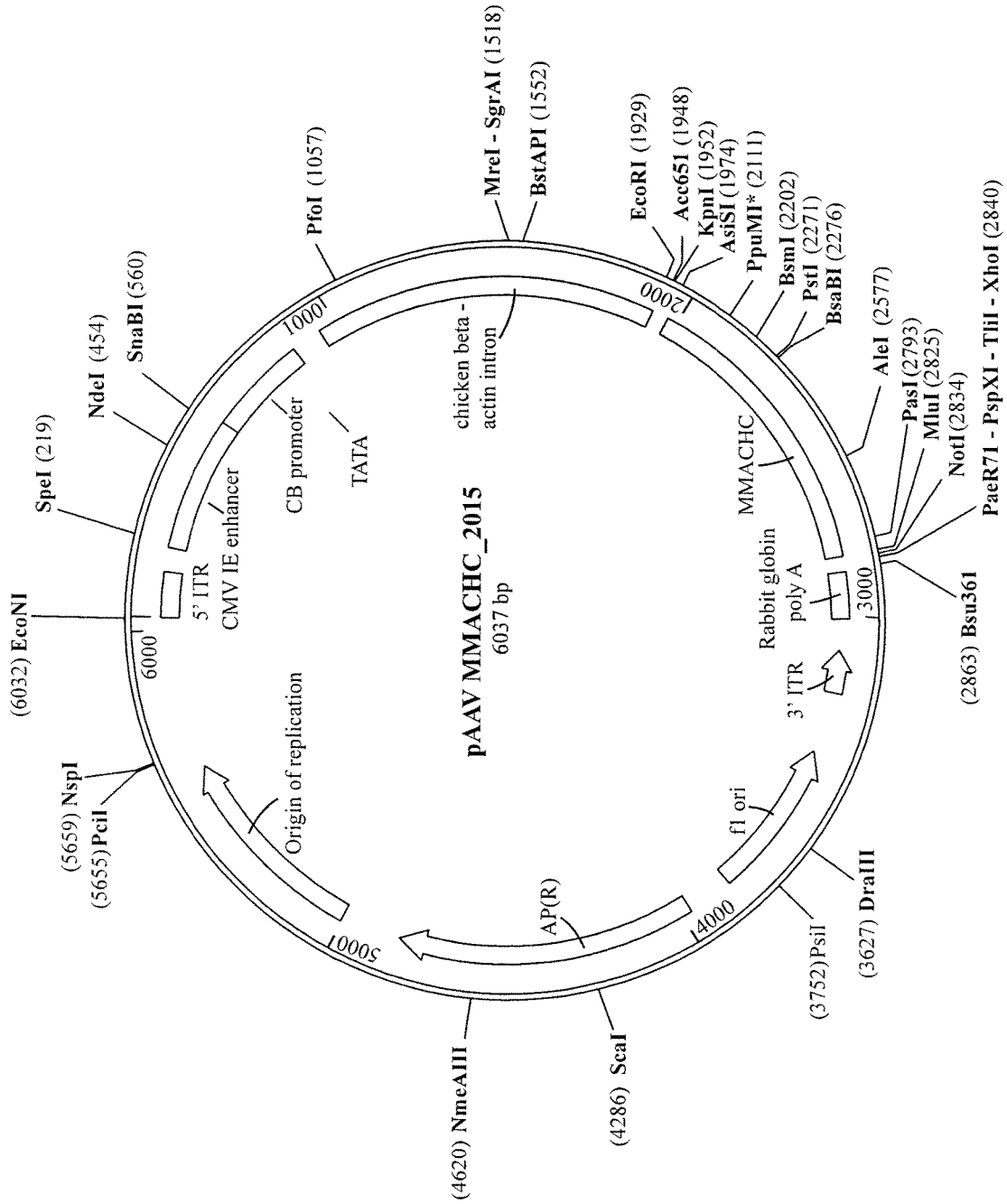
FIGS. 9A-9E are diagrams showing AAV (Adeno-Associated Virus) vector maps.
Figure 9B:
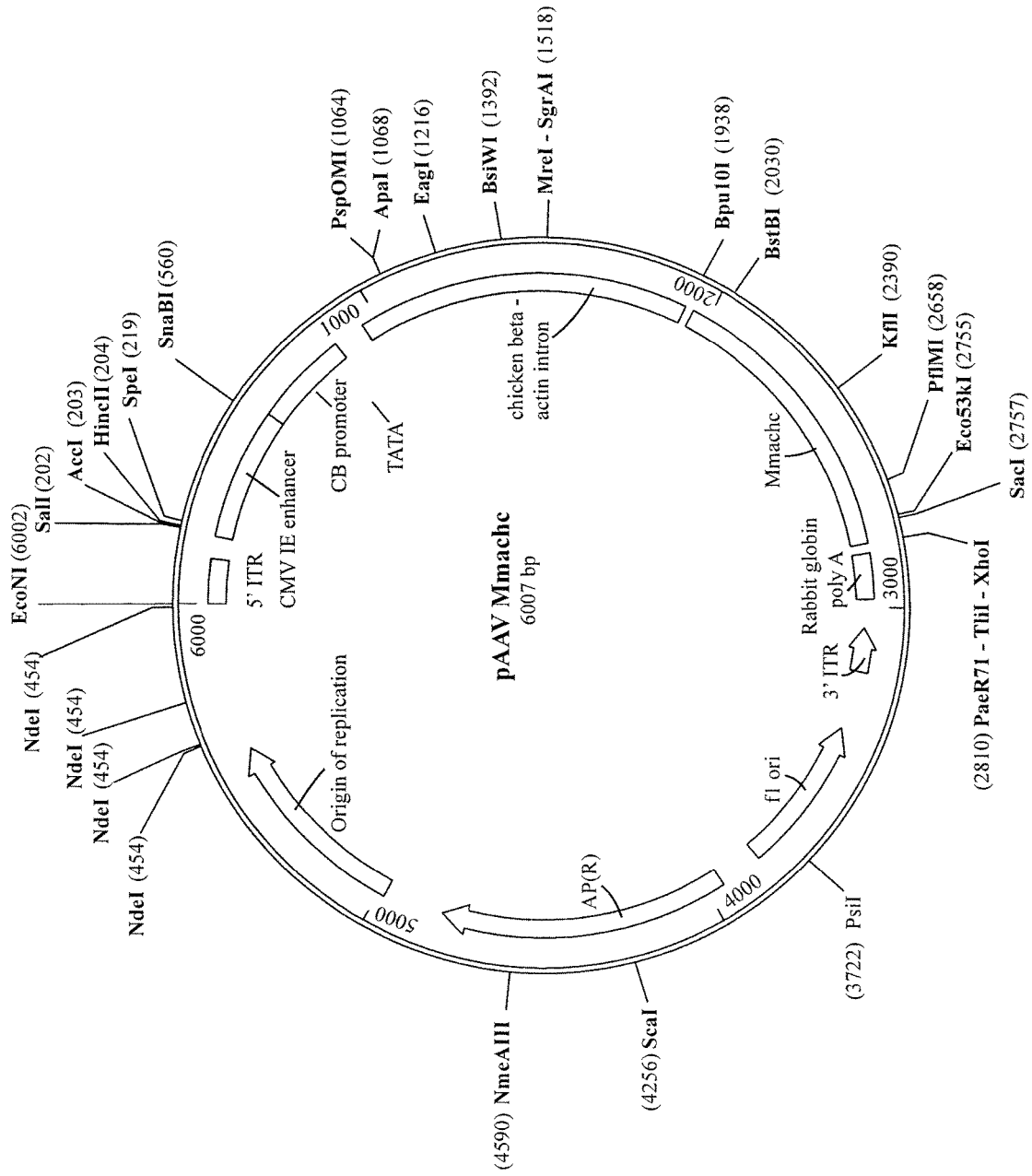
Figure 9C:
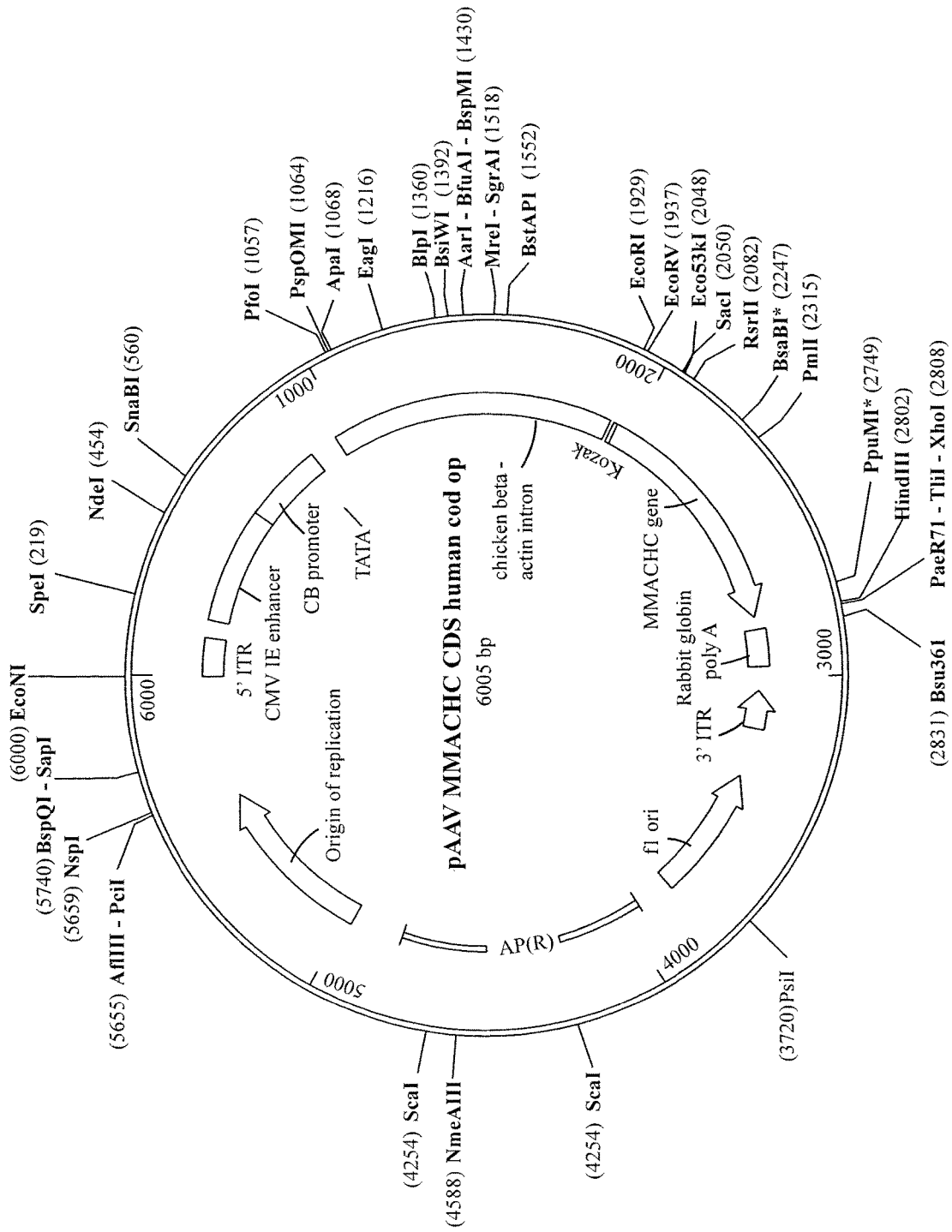
Figure 9D:
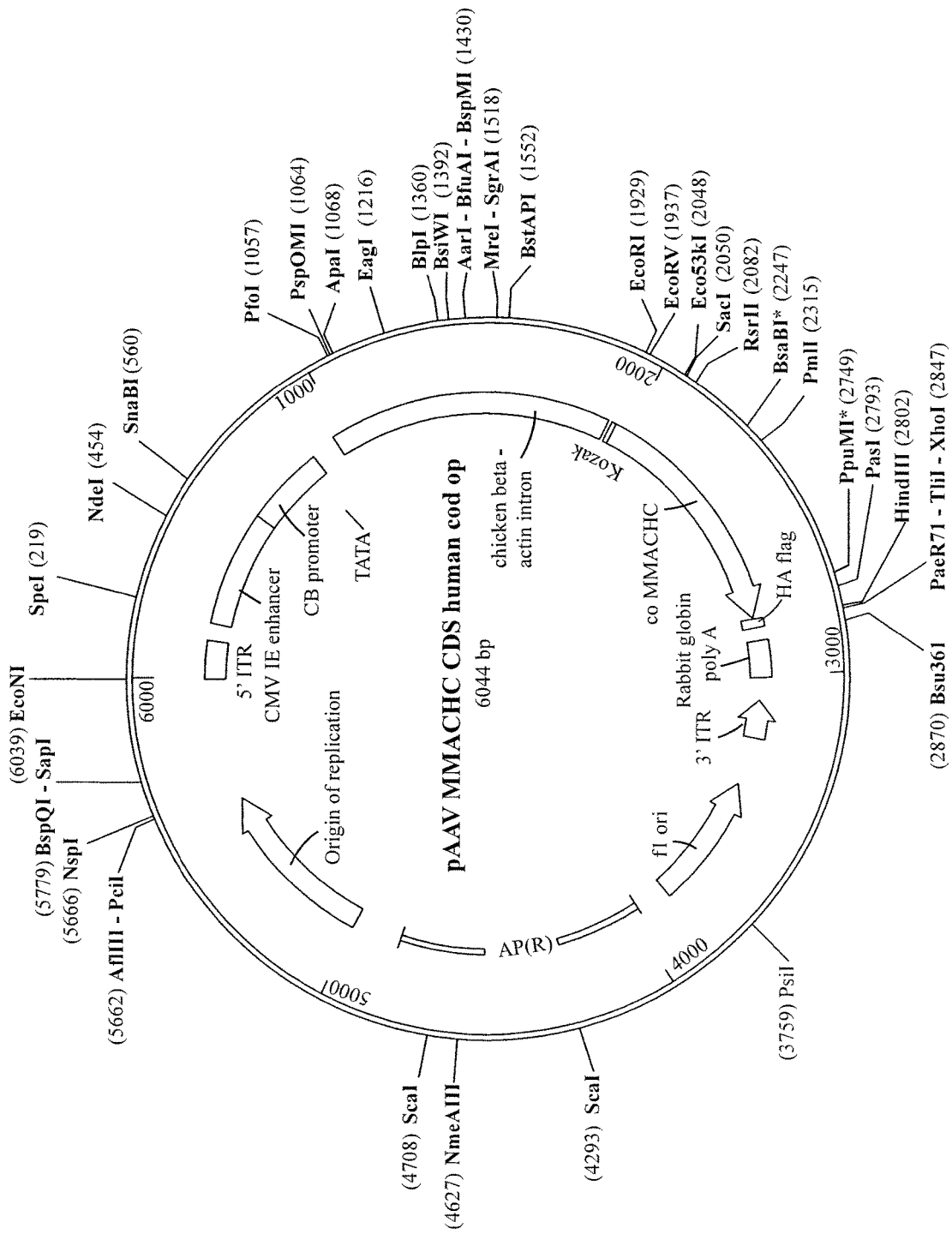
Figure 9E:
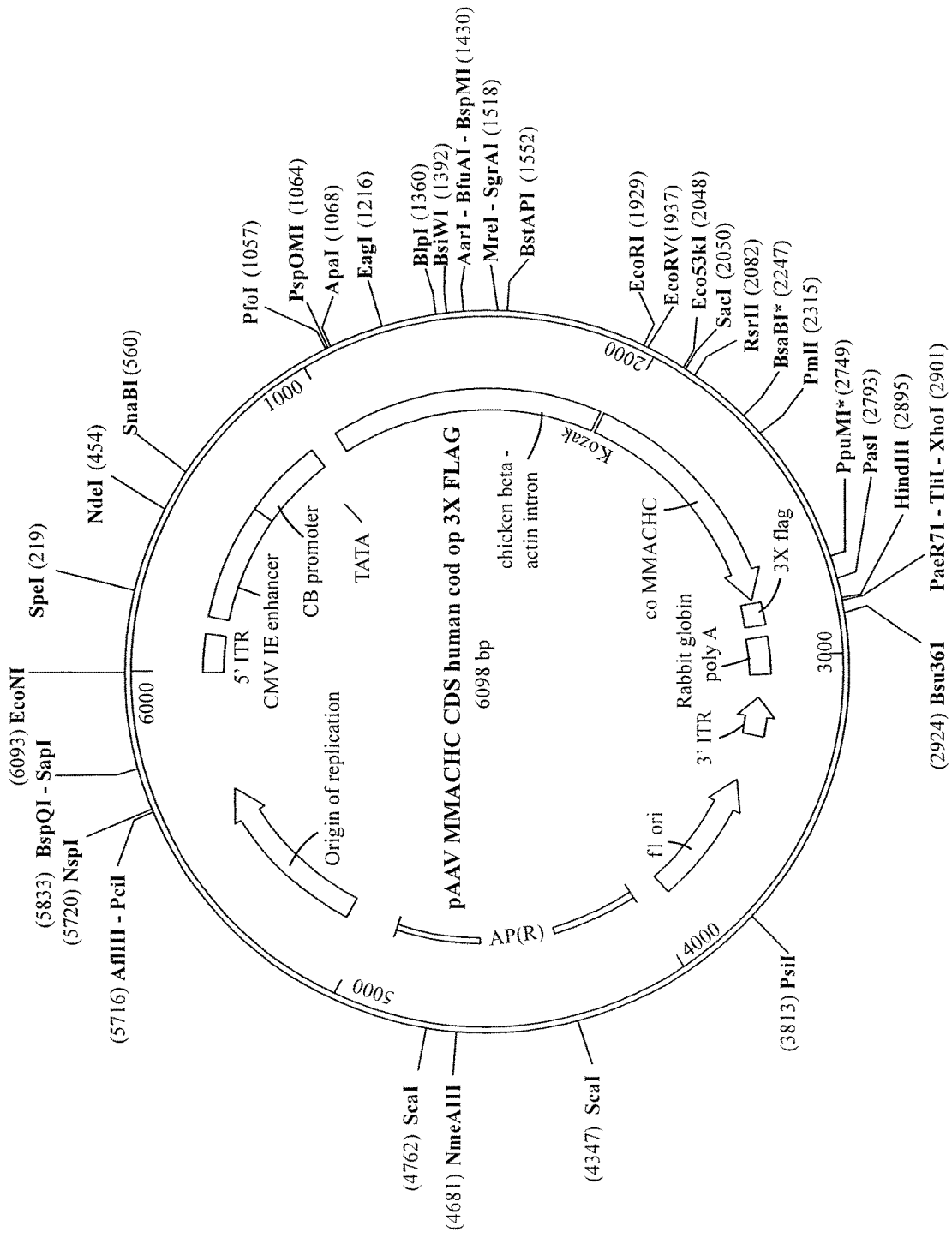

Adeno-associated viruses (AAVs) were constructed that were designed to broadly express either (i) the wild-type human MMACHC (SEQ ID NO: 1, and having stop codon TAA); (ii) the wild-type mouse Mmachc (SEQ ID NO: 10, and having stop codon TAA); (iii) a codon-optimized, synthetic human MMACHC (SEQ ID NO: 2, and having stop codons TAA and TGA; (iv) a codon-optimized, synthetic human MMACHC tagged with hemagglutinin (HA) (SEQ ID NO: 11, and having stop codons TAA and TGA; or (v) a codon-optimized, synthetic human MMACHC tagged with 3xFLAG (SEQ ID NO: 12, and having stop codons TAA and TGA. All constructs were under the control of the enhanced chicken beta actin promoter (CBA). Each plasmid at 2.5 micrograms was transfected into 293T cells, the cells were harvested and immunoreactive MMACHC was detected with two distinct MMACHC antibodies by Western blotting. FIGS. 8A and 8B show increased expression of the codon-optimized alleles compared to the wild-type Mmachc. FIG. 8C shows the specificity of the HA tag, and FIG. 8D shows the specificity of the FLAG tag.

EXAMPLE 4

This example demonstrates the development of gene therapies for cblC.

Adeno-associated viruses (AAVs) were constructed that were designed to broadly express either (i) the wild-type human MMACHC (SEQ ID NO: 1, and having stop codon TAA); (ii) the wild-type mouse Mmachc (SEQ ID NO: 10, and having stop codon TAA, in rh10 serotype; vector termed AAVrh10-CBA-Mmachc); (iii) a codon-optimized, synthetic human MMACHC (SEQ ID NO: 2, and having stop codons TAA and TGA, in AAV9 serotype; vector termed AAV9-CBA-coMMACHC); (iv) a codon-optimized, synthetic human MMACHC tagged with hemagglutinin (HA) (SEQ ID NO: 11, and having stop codons TAA and TGA; or (v) a codon-optimized, synthetic human MMACHC tagged with 3xFLAG (SEQ ID NO: 12, and having stop codons TAA and TGA. All constructs were under the control of the enhanced chicken beta actin promoter (CBA). The recombinant AAVs were pseudotyped with an rh10 or type 9 capsid and delivered to mice in the early natal period by direct liver injection. The AAV sequences corresponding to (i)-(v) are at SEQ ID NOS: 5-9, respectively, and are diagrammatically shown at FIGS. 9A-9E, respectively.

AAVs based on the vectors (ii) and (iii) above were produced in vitro, and mice received a single intrahepatic injection of $1 \times 10^{11}$ genome copies of AAV (ii) or (iii) per mouse at postnatal day 0-2 using previously described methods (Chandler et al., Mol. Ther., 18(1):11-16 (2010), incorporated by reference herein in its entirety).

Figure 10:
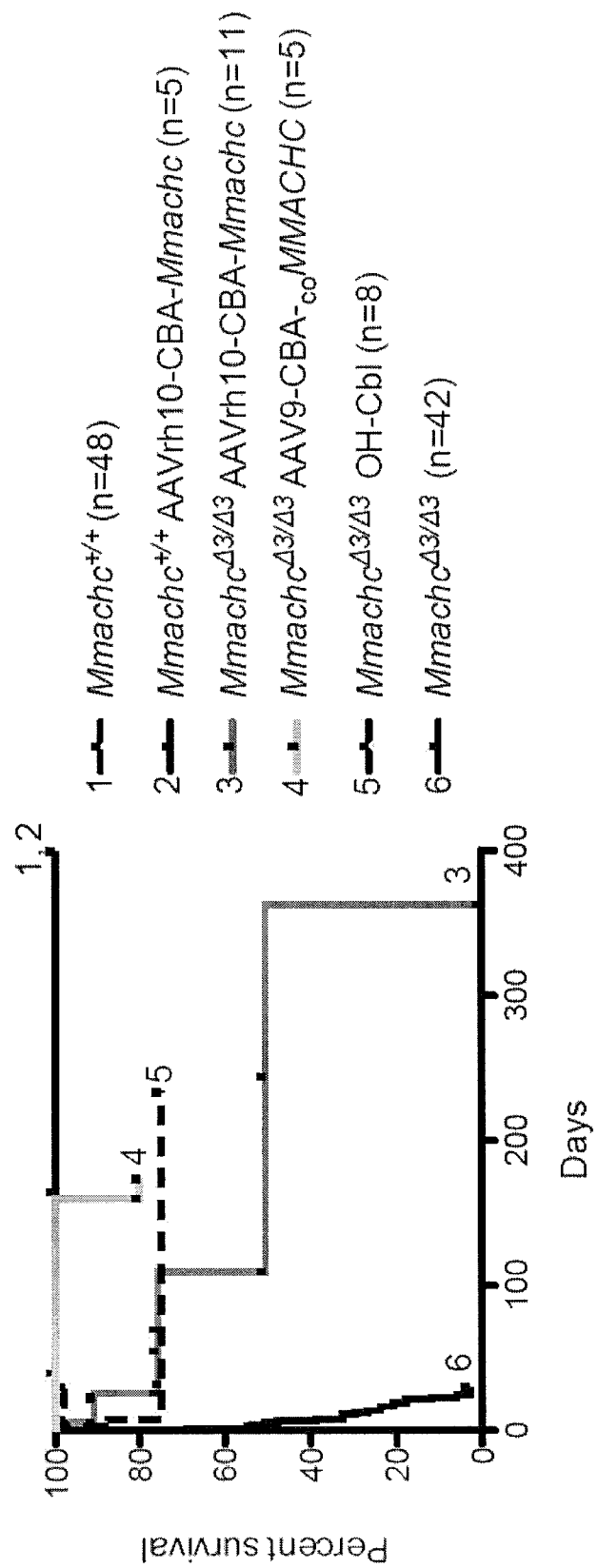
FIG. 10 is a line graph showing neonatal treatment with AAVrh10-CBA-Mmachc or AAV9-CBA-coMMACHC improves survival of Mmachc$^{Δ3/Δ3}$ mice, in accordance with embodiments of the invention (**** p<0.0001, compared to untreated Mmachc$^{Δ3/Δ3}$). The treated mice have about 80% survival at 100 days after a single neonatal injection compared with the untreated mice which do not survive.

After one month, when 100% of untreated mice had perished, greater than 75% of the treated Mmachc$^{\Delta 3/\Delta 3}$ mice were alive and the long term survival (6 months) was greater than 50% (FIG. 10). Of note, the mice treated with the AAV 9 vector that expresses the codon-optimized MMACHC, 100% were alive greater than 60 days, with improved clinical appearance. Mmachc$^{\Delta 3/\Delta 3}$ mice treated with AAV vectors (AAVrh10 n=11, AAV9 n=5) displayed dramatically improved clinical appearance with improved growth (p=0.0568), and increased survival (p<0.0001 for both vectors), with the oldest treated mutants living beyond 9 months.

The gene therapies appear more effective than OH-cbl injections in terms of survival. FIG. 10 also shows the OH-Cbl treatment of Mmachc$^{\Delta 3/\Delta 3}$ mice.

Figure 11:
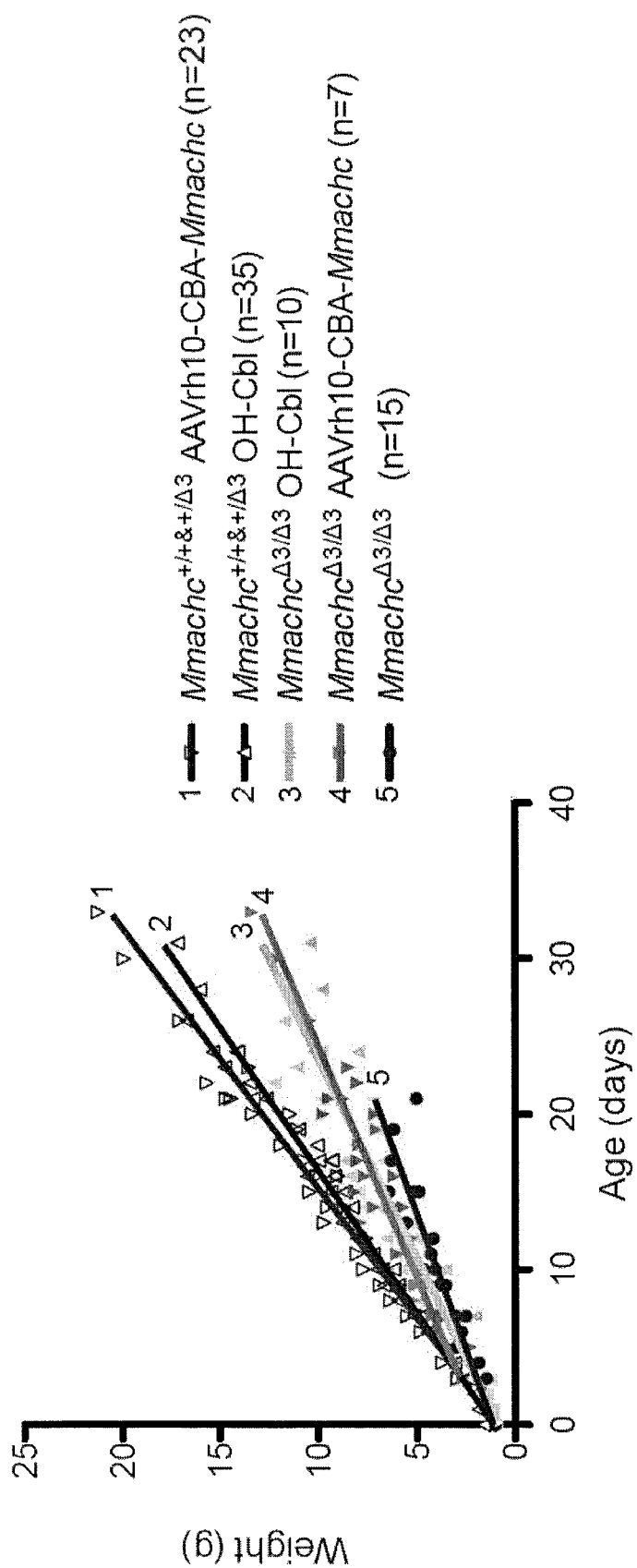
FIG. 11 is a line graph showing that the AAVrh10-CBA-Mmachc treated Mmachc$^{Δ3/Δ3}$ mice (group 4) have improved weight gain in the first month of life compared with untreated mice (group 5). AAVrh10-CBA-Mmachc treated Mmachc$^{Δ3/Δ3}$ mice are essentially identical in weight to those that receive OH-Cbl 1-2 times per week (group 3) but remain smaller than wild-type and heterozygous mice.

Gene therapy (GT) treated Mmachc$^{\Delta 3/\Delta 3}$ mice remain small (FIG. 11), and hypopigmentation in a gene therapy treated mouse increases over time, but achieve the same growth parameters as those treated by tri-weekly OH-cbl injections.

Figure 12:
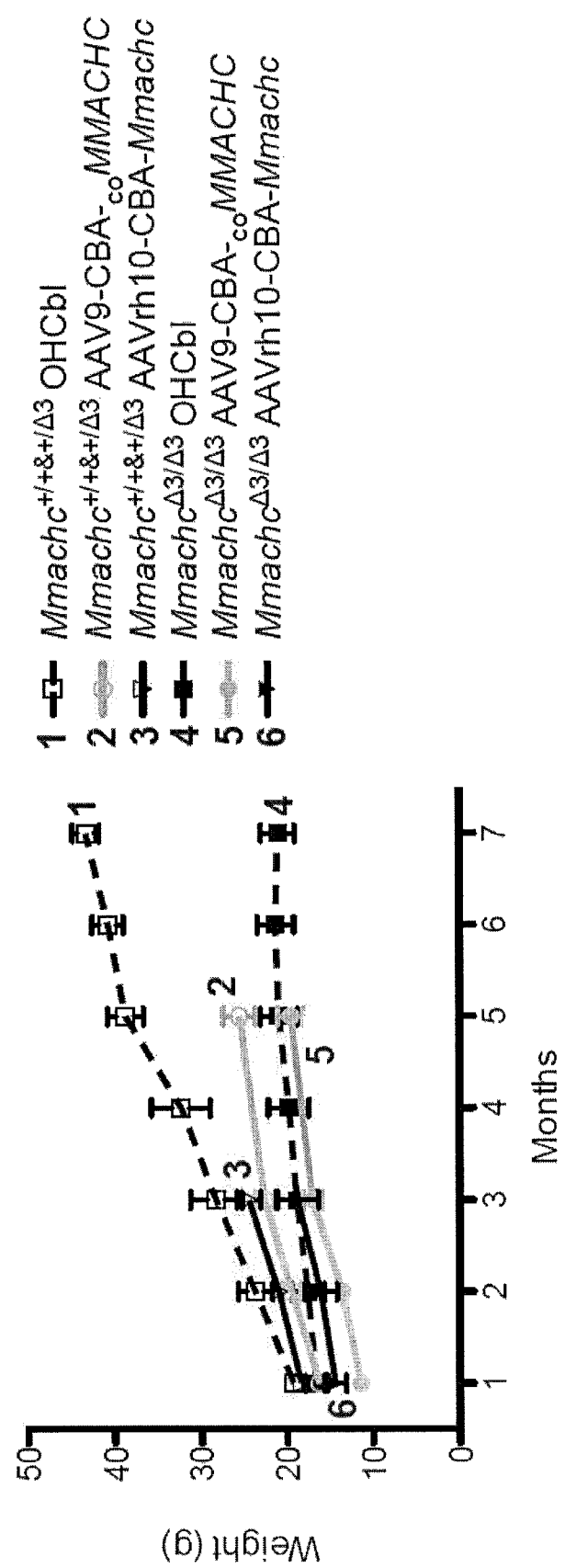
FIG. 12 is a line graph showing the weights of the Mmachc$^{Δ3/Δ3}$ mice treated with OH-Cbl, AAVrh10-CBA-Mmachc or AAV9-CBA-coMMACHC over time. Mmachc$^{Δ3/Δ3}$ mice treated with a single injection of AAV in the neonatal period are essentially identical in weight to those that receive OH-Cbl 1-2 times per week. All Mmachc$^{Δ3/Δ3}$ mutant mice remain smaller than wild-type and heterozygous mice.

Mmachc mice were treated with OHcbl 1-2 times per week or a single injection of AAV9-CBA-coMMACHC or AAVrh10-CBA-Mmachc and weighed monthly (FIG. 12). For this study, the animals were maintained on a high fat, fruit, and enterocal enriched diet because of previous work suggesting that such a diet may aid in the survival of animals with isolated methylmalonic acidemia (Chandler et al, FASEB J, 23:1252-61 (2009)). The prolonged intake of such a high fat, carbohydrate enriched diet can cause unaffected or Mmachc carriers to develop increased weight gain and obesity, which explains why the control and heterozygous mice (Group 1, FIG. 12) in this specific study are much larger than the treated mutants or other controls after 7 months ingesting this diet, as compared to the 40 day old mice control mice presented in FIG. 11 (Group 1).

A small number of mice treated with gene therapy were sacrificed for ocular studies. The mice display thinning of the outer segments and a retinopathy that is similar to what has been described in humans. Specifically, there was a loss of inner and outer photoreceptors and thinning of the outer nuclear layer, with a reduced number of cells in the outer nuclear layer and shortening of photoreceptor outer segments. Hence, gene therapy was used to create cblC mice that then survive long enough to display the eye disease, which can then be further treated by the invention described herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Also, everywhere "comprising" (or its equivalent) is recited, the "comprising" is considered to incorporate "consisting essentially of" and "consisting of." Thus, an embodiment "comprising" (an) element(s) supports embodiments "consisting essentially of" and "consisting of" the recited element(s). Everywhere "consisting essentially of" is recited is considered to incorporate "consisting of." Thus, an embodiment "consisting essentially of" (an) element(s) supports embodiments "consisting of" the recited element(s). "Consisting essentially of" limits the scope of a claim to the specified materials or steps and those that do not materially affect the basic and novel characteristic(s) of the claim.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A synthetic methylmalonic aciduria cblC type and homocystinuria type C protein (MMACHC) polynucleotide comprising a polynucleotide encoding MMACHC that is codon-optimized for expression in a human, wherein the polynucleotide encoding MMACHC comprises the sequence of SEQ ID NO: 2.

2. The synthetic MMACHC polynucleotide of claim 1, wherein the polynucleotide further comprises a polynucleotide encoding at least one of a hemagglutinin tag and a 3×FLAG tag.

3. A composition comprising the synthetic MMACHC polynucleotide of claim 1 and a pharmaceutically acceptable carrier.

4. An expression vector comprising the synthetic MMACHC polynucleotide of claim 1.

5. The expression vector of claim 4, wherein the synthetic MMACHC polynucleotide is under the control of a chicken beta actin (CBA) promoter.

6. The expression vector of claim 4, wherein the expression vector is a viral vector.

7. The expression vector of claim 6, wherein the viral vector is an adeno-associated viral (AAV) vector.

8. The expression vector of claim 7, wherein the AAV is pseudotyped with at least one of rh10, type 9, type 8, and 7m8 capsid.

9. The expression vector comprising an isolated nucleic acid sequence selected from the group consisting of the nucleotide of SEQ ID NO:5, SEQ ID NO:6, SEQ ID NO:7, SEQ ID NO:8 and SEQ ID NO:9.

10. The expression vector of claim 9, wherein the expression vector comprises the nucleic acid sequence of SEQ ID NO: 5.

11. The expression vector of claim 9, wherein the expression vector comprises the nucleic acid sequence of SEQ ID NO: 6.

12. The expression vector of claim 9, wherein the expression vector comprises the nucleic acid sequence of SEQ ID NO: 7.

13. The expression vector of claim 9, wherein the expression vector comprises the nucleic acid sequence of SEQ ID NO: 8.

14. The expression vector of claim 9, wherein the expression vector comprises the nucleic acid sequence of SEQ ID NO: 9.

* * * * *

SEQUENCE LISTING

```
<160> NUMBER OF SEQ ID NOS: 12

<210> SEQ ID NO 1
<211> LENGTH: 846
<212> TYPE: DNA
<213> ORGANISM: Homo sapiens
<220> FEATURE:
<221> NAME/KEY: misc_feature
<223> OTHER INFORMATION: wild-type human MMACHC

<400> SEQUENCE: 1
atggagccga aagtcgcaga gctgaagcag aagatcgagg acacgctatg tccttttggc      60
ttcgaggttt accccttcca ggtggcatgg tacaatgaac tcttgcctcc agccttccac     120
ctaccgctgc caggacctac cctggccttc ctggtactca gcacgcctgc catgtttgac     180
cgggccctca agcccttctt gcagagctgc cacctccgaa tgctgactga cccagtggac     240
cagtgtgtgg cctaccatct gggccgtgtt agagagagcc tcccagagct gcagatagaa     300
atcattgctg actacgaggt gcaccccaac cgacgcccca agatcctggc ccagacagca     360
gcccatgtag ctggggctgc ttactactac caacgacaag atgtggaggc tgacccatgg     420
gggaaccagc gcatatcagg tgtgtgcata caccccgat ttggggctg gtttgccatc      480 cgaggggtag tgctgctgcc agggatagag gtgccagatc tgccacccag aaaacctcat     540
gactgtgtac ctacaagagc tgaccgtatc gccctactcg aaggcttcaa tttccactgg     600
```

| | |
|---|---|
| cgtgattgga cttaccggga tgctgtgaca ccccaggagc gctactcaga agagcagaag | 660 |
| gcctacttct ccactccacc tgcccaacga ttggccctat tgggcttggc tcagccctca | 720 |
| gagaagccta gttctccctc cccggacctt ccctttacca cacccgcccc caagaagcct | 780 |
| gggaatccca gcagagcccg gagctggctc agcccaggg tctcaccacc tgcatcccct | 840 |
| ggccct | 846 |

```
<210> SEQ ID NO 2
<211> LENGTH: 846
<212> TYPE: DNA
<213> ORGANISM: Homo sapiens
<220> FEATURE:
<221> NAME/KEY: misc_feature
<223> OTHER INFORMATION: codon optimized human MMACHC

<400> SEQUENCE: 2
```

| | |
|---|---|
| atggaaccta aagtcgcaga actcaagcag aagatcgagg acaccctgtg cccgttcgga | 60 |
| ttcgaggtgt acccttttcca agtggcctgg tacaacgagc tcctgccccc tgctttccat | 120 |
| ttgccactgc ccgtccgac tctcgcgttt cttgtgctgt cgaccccgc gatgttcgac | 180 |
| cgcgccctca gccgttcct gcaatcatgt catctgcgga tgctgaccga tccggtcgat | 240 |
| cagtgcgtgg cctaccacct gggtcgcgtc agggaatccc tgccggagct tcagatcgag | 300 |
| atcatcgcgg attacgaagt gcacccaaac cggcggccca agattctcgc caaaccgcc | 360 |
| gcgcacgtgg ctggcgccgc ctattactac cagcgccagg acgtcgaggc ggacccttgg | 420 |
| ggcaatcaga gaatctctgg agtgtgcatc cacccacggt tcgggggatg gttcgcaatt | 480 |
| cggggcgtgg tgctgctgcc gggaatcgag gtgccagact tgcctcctcg aaagccccac | 540 |
| gactgcgtgc caactagagc cgatagaatt gccctgctgg aagggttcaa cttccattgg | 600 |
| cgcgactgga cctaccggga cgctgtgact cctcaagaac gctacagcga gaacagaag | 660 |
| gcctactttt caactccgcc ggcccagcgc ctggcactcc tgggactggc ccagccctcc | 720 |
| gagaagccta gctccccctc gccggacttg cccttcacca cccggcccc caaaaagccc | 780 |
| ggcaacccta gccgggccag gtcctggctg tccccgaggg tgtccccgcc tgcctccccc | 840 |
| ggccct | 846 |

```
<210> SEQ ID NO 3
<211> LENGTH: 27
<212> TYPE: DNA
<213> ORGANISM: Artificial Sequence
<220> FEATURE:
<223> OTHER INFORMATION: hemagglutinin (HA) tag

<400> SEQUENCE: 3
```

| | |
|---|---|
| tacccgtatg atgtgcccga ctacgcc | 27 |

```
<210> SEQ ID NO 4
<211> LENGTH: 81
<212> TYPE: DNA
<213> ORGANISM: Artificial Sequence
<220> FEATURE:
<223> OTHER INFORMATION: 3xFLAG tag

<400> SEQUENCE: 4
```

| | |
|---|---|
| gactacaaag atgacgacga caaggagac tataaggacg acgacgataa gggagattac | 60 |
| aaggatgacg atgacaaggg c | 81 |

```
<210> SEQ ID NO 5
<211> LENGTH: 6037
<212> TYPE: DNA
<213> ORGANISM: Artificial Sequence
<220> FEATURE:
<223> OTHER INFORMATION: AAV with wild-type human MMACHC

<400> SEQUENCE: 5
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120
taggggttcc ttgtagttaa tgattaaccc gccatgctac ttatctacca gggtaatggg     180
gatcctctag aactatagct agtcgacatt gattattgac tagttattaa tagtaatcaa     240
ttacggggtc attagttcat agcccatata tggagttccg cgttacataa cttacggtaa     300
atggcccgcc tggctgaccg cccaacgacc cccgcccatt gacgtcaata atgacgtatg     360
ttcccatagt aacgccaata gggactttcc attgacgtca atgggtggag tatttacggt     420
aaactgccca cttggcagta catcaagtgt atcatatgcc aagtacgccc cctattgacg     480
tcaatgacgg taaatggccc gcctggcatt atgcccagta catgacctta tgggactttc     540
ctacttggca gtacatctac gtattagtca tcgctattac catggtcgag gtgagcccca     600
cgttctgctt cactctcccc atctcccccc cctccccacc cccaattttg tatttattta     660
ttttttaatt attttgtgca gcgatggggg cggggggggg ggggggcgc gcgccaggcg     720 ggcggggcg gggcgagggg cggggcgggg cgaggcggag aggtgcggcg gcagccaatc     780
agagcggcgc gctccgaaag tttccttttta tggcgaggcg gcggcggcgg cggccctata     840
aaaagcgaag cgcgcggcgg gcgggagtcg ctgcgcgctg ccttcgcccc gtgccccgct     900
ccgccgccgc ctcgcgccgc ccgccccggc tctgactgac cgcgttactc ccacaggtga     960
gcgggcggga cggcccttct cctccgggct gtaattagcg cttggtttaa tgacggcttg    1020
tttcttttct gtggctgcgt gaaagccttg aggggctccg ggagggccct ttgtgcgggg    1080
ggagcggctc ggggggtgcg tgcgtgtgtg tgtgcgtggg gagcgccgcg tgcggctccg    1140
cgctgcccgg cggctgtgag cgctgcgggc gcggcgcggg gctttgtgcg ctccgcagtg    1200
tgcgcgaggg gagcgcggcc ggggcggtg ccccgcggtg cggggggggc tgcgagggga    1260
acaaaggctg cgtgcggggt gtgtgcgtgg gggggtgagc aggggggtgtg ggcgcgtcgg    1320 tcgggctgca acccccccctg cacccccctc cccgagttgc tgagcacggc ccggcttcgg    1380
gtgcggggct ccgtacgggg cgtggcgcgg ggctcgccgt gccgggcggg gggtggcggc    1440
aggtgggggt gccgggcggg gcggggccgc ctcgggccgg ggagggctcg ggggagggc    1500 gcggcggccc ccggagcgcc ggcggctgtc gaggcgcggc gagccgcagc cattgccttt    1560
tatggtaatc gtgcgagagg gcgcaggac ttcctttgtc ccaaatctgt gcggagccga    1620
aatctgggag gcgccgccgc accccctcta gcgggcgcgg ggcgaagcgg tgcggcgccg    1680
gcaggaagga aatgggcggg gagggcctttc gtgcgtcgcc gcgccgccgt ccccttctcc    1740
ctctccagcc tcggggctgt ccgcgggggg acggctgcct tcgggggga cggggcaggg    1800 cggggttcgg cttctggcgt gtgaccggcg gctctagagc ctctgctaac catgttcatg    1860
ccttcttctt tttcctacag ctcctgggca acgtgctggt tattgtgctg tctcatcatt    1920
ttggcaaaga attcgtcgac tggatccggt accgaggaga tctgccgccg cgatcgccat    1980
ggagccgaaa gtcgcagagc tgaagcagaa gatcgaggac acgctatgtc cttttggctt    2040
cgaggtttac cccttccagg tggcatggta caatgaactc ttgcctccag ccttccacct    2100
```

```
accgctgcca ggacctaccc tggccttcct ggtactcagc acgcctgcca tgtttgaccg    2160
ggccctcaag cccttcttgc agagctgcca cctccgaatg ctgactgacc cagtggacca    2220
gtgtgtggcc taccatctgg gccgtgttag agagagcctc ccagagctgc agatagaaat    2280
cattgctgac tacgaggtgc accccaaccg acgcccaag atcctggccc agacagcagc     2340
ccatgtagct ggggctgctt actactacca acgacaagat gtggaggctg acccatgggg    2400
gaaccagcgc atatcaggtg tgtgcataca ccccgattt gggggctggt ttgccatccg     2460
aggggtagtg ctgctgccag ggatagaggt gccagatctg ccacccagaa aacctcatga    2520
ctgtgtacct acaagagctg accgtatcgc cctactcgaa ggcttcaatt tccactggcg    2580
tgattggact taccgggatg ctgtgacacc ccaggagcgc tactcagaag agcagaaggc    2640
ctacttctcc actccacctg cccaacgatt ggccctattg gcttggctc agccctcaga     2700 gaagcctagt tctccctccc cggaccttcc ctttaccaca cccgccccca agaagcctgg    2760
gaatcccagc agagcccgga gctggctcag ccccagggtc tcaccacctg catccctgg    2820 ccctacgcgt acgcggccgc tcgaggacgg ggtgaactac gcctgaggat ccgatctttt    2880
tccctctgcc aaaaattatg gggacatcat gaagcccctt gagcatctga cttctggcta    2940 ataaggaaa tttattttca ttgcaatagt gtgttggaat ttttttgtgtc tctcactcgg    3000 aagcaattcg ttgatctgaa tttcgaccac ccataatacc cattaccctg gtagataagt    3060 agcatgcgg gttaatcatt aactacaagg aaccccctagt gatggagttg gccactccct   3120
ctctgcgcgc tcgctcgctc actgaggccg gcgaccaaa ggtcgcccga cgcccgggct    3180
ttgcccgggg ggcctcagtg agcgagcgag cgcgcagcct taattaacct aattcactgg    3240
ccgtcgtttt acaacgtcgt gactgggaaa accctggcgt tacccaactt aatcgccttg    3300
cagcacatcc ccctttcgcc agctggcgta atagcgaaga ggcccgcacc gatcgccctt    3360
cccaacagtt gcgcagcctg aatggcgaat gggacgcgcc ctgtagcggc gcattaagcg    3420
cggcgggtgt ggtggttacg cgcagcgtga ccgctacact tgccagcgcc ctagcgcccg    3480
ctcctttcgc tttcttccct tcctttctcg ccacgttcgc cggctttccc cgtcaagctc    3540
taaatcgggg gctcccttta gggttccgat ttagtgcttt acggcacctc gaccccaaaa    3600
aacttgatta gggtgatggt tcacgtagtg gccatcgccc tgatagacg gttttcgcc     3660 ctttgacgtt ggagtccacg ttctttaata gtggactctt gttccaaact ggaacaacac    3720
tcaaccctat ctcggtctat cttttgatt tataagggat tttgccgatt tcggcctatt     3780
ggttaaaaaa tgagctgatt taacaaaaat ttaacgcgaa ttttaacaaa atattaacgc    3840
ttacaattta ggtggcactt ttcggggaaa tgtgcgcgga accctatt gtttattttt     3900 ctaaatacat tcaaatatgt atccgctcat gagacaataa ccctgataaa tgcttcaata    3960
atattgaaaa aggaagagta tgagtattca acatttccgt gtcgccctta ttccctttt    4020 tgcggcattt tgccttcctg ttttttgctca cccagaaacg ctggtgaaag taaaagatgc   4080
tgaagatcag ttgggtgcac gagtgggtta catcgaactg gatctcaaca gcggtaagat    4140
ccttgagagt tttcgccccg aagaacgttt tccaatgatg agcacttta aagttctgct     4200 atgtggcgcg gtattatccc gtattgacgc cgggcaagag caactcggtc gccgcataca    4260
ctattctcag aatgacttgg ttgagtactc accagtcaca gaaaagcatc ttacggatgg    4320
catgacagta agagaattat gcagtgctgc cataaccatg agtgataaca ctgcggccaa    4380
cttacttctg acaacgatcg gaggaccgaa ggagctaacc gcttttttgc acaacatggg    4440
ggatcatgta actcgccttg atcgttggga accggagctg aatgaagcca taccaaacga    4500
```

```
cgagcgtgac accacgatgc ctgtagcaat ggcaacaacg ttgcgcaaac tattaactgg    4560
cgaactactt actctagctt cccggcaaca attaatagac tggatggagg cggataaagt    4620
tgcaggacca cttctgcgct cggcccttcc ggctggctgg tttattgctg ataaatctgg    4680
agccggtgag cgtgggtctc gcggtatcat tgcagcactg gggccagatg gtaagccctc    4740
ccgtatcgta gttatctaca cgacggggag tcaggcaact atggatgaac gaaatagaca    4800
gatcgctgag ataggtgcct cactgattaa gcattggtaa ctgtcagacc aagtttactc    4860
atatatactt tagattgatt taaaacttca ttttaatttt aaaaggatct aggtgaagat    4920
cctttttgat aatctcatga ccaaaatccc ttaacgtgag ttttcgttcc actgagcgtc    4980
agaccccgta gaaaagatca aaggatcttc ttgagatcct ttttttctgc gcgtaatctg    5040
ctgcttgcaa acaaaaaaac caccgctacc agcggtggtt tgtttgccgg atcaagagct    5100
accaactctt tttccgaagg taactggctt cagcagagcg cagataccaa atactgttct    5160
tctagtgtag ccgtagttag gccaccactt caagaactct gtagcaccgc ctacatacct    5220
cgctctgcta atcctgttac cagtggctgc tgccagtggc gataagtcgt gtcttaccgg    5280
gttggactca agacgatagt taccggataa ggcgcagcgg tcgggctgaa cggggggttc    5340
gtgcacacag cccagcttgg agcgaacgac ctacaccgaa ctgagatacc tacagcgtga    5400
gctatgagaa agcgccacgc ttcccgaagg gagaaaggcg gacaggtatc cggtaagcgg    5460
cagggtcgga acaggagagc gcacgaggga gcttccaggg ggaaacgcct ggtatcttta    5520
tagtcctgtc gggtttcgcc acctctgact tgagcgtcga ttttttgtgat gctcgtcagg    5580 ggggcggagc ctatggaaaa acgccagcaa cgcggccttt ttacggttcc tggccttttg    5640
ctggcctttt gctcacatgt tctttcctgc gttatcccct gattctgtgg ataaccgtat    5700
taccgccttt gagtgagctg ataccgctcg ccgcagccga acgaccgagc gcagcgagtc    5760
agtgagcgag gaagcggaag agcgcccaat acgcaaaccg cctctccccg cgcgttggcc    5820
gattcattaa tgcagctggc acgacaggtt cccgactgg aaagcgggca gtgagcgcaa    5880
cgcaattaat gtgagttagc tcactcatta ggcaccccag gctttacact ttatgcttcc    5940
ggctcgtatg ttgtgtggaa ttgtgagcgg ataacaattt cacacaggaa acagctatga    6000
ccatgattac gccagattta attaaggcct taattag                            6037
```

<210> SEQ ID NO 6
<211> LENGTH: 6007
<212> TYPE: DNA
<213> ORGANISM: Artificial Sequence
<220> FEATURE:
<223> OTHER INFORMATION: AAV with wild-type mouse Mmachc

<400> SEQUENCE: 6

```
gctgcgcgct cgctcgctca ctgaggccgc ccgggcaaag cccgggcgtc gggcgacctt     60
tggtcgcccg gcctcagtga gcgagcgagc gcgcagagag ggagtggcca actccatcac    120
taggggttcc ttgtagttaa tgattaaccc gccatgctac ttatctacca gggtaatggg    180
gatcctctag aactatagct agtcgacatt gattattgac tagttattaa tagtaatcaa    240
ttacggggtc attagttcat agcccatata tggagttccg cgttacataa cttacggtaa    300
atggcccgcc tggctgaccg cccaacgacc cccgcccatt gacgtcaata atgacgtatg    360
ttcccatagt aacgccaata gggactttcc attgacgtca atgggtggag tatttacggt    420
aaactgccca cttggcagta catcaagtgt atcatatgcc aagtacgccc cctattgacg    480
```

```
tcaatgacgg taaatggccc gcctggcatt atgcccagta catgacctta tgggactttc     540
ctacttggca gtacatctac gtattagtca tcgctattac catggtcgag gtgagcccca     600
cgttctgctt cactctcccc atctccccce cctccccacc cccaattttg tatttattta     660 tttttaatt attttgtgca gcgatggggg cggggggggg ggggggggcgc gcgccaggcg     720 gggcggggcg gggcgagggg cggggcgggg cgaggcggag aggtgcggcg gcagccaatc     780
agagcggcgc gctccgaaag tttccttta tggcgaggcg gcggcggcgg cggccctata     840
aaaagcgaag cgcgcggcgg gcgggagtcg ctgcgcgctg ccttcgcccc gtgcccgct      900 ccgccgccgc ctcgcgccgc ccgccccggc tctgactgac cgcgttactc ccacaggtga     960
gcgggcggga cggcccttct cctccgggct gtaattagcg cttggtttaa tgacggcttg    1020
tttcttttct gtggctgcgt gaaagccttg aggggctccg ggagggccct ttgtgcgggg    1080
ggagcggctc gggggtgcg tgcgtgtgtg tgtgcgtggg gagcgccgcg tgcggctccg    1140
cgctgcccgg cggctgtgag cgctgcgggc gcggcgcggg gctttgtgcg ctccgcagtg    1200
tgcgcgaggg gagcgcggcc gggggcggtg ccccgcggtg cgggggggggc tgcgagggga   1260 acaaaggctg cgtgcggggt gtgtgcgtgg ggggtgagc aggggtgtg ggcgcgtcgg     1320 tcgggctgca accccccctg caccccccct cccgagttgc tgagcacggc ccggcttcgg    1380
gtgcggggct ccgtacgggg cgtggcgcgg ggctcgccgt gccgggcggg gggtggcggc    1440
aggtgggggt gccgggcggg gcggggccgc ctcgggccgg ggagggctcg ggggagggc   1500 gcggcggccc ccggagcgcc ggcggctgtc gaggcgcggc gagccgcagc cattgccttt    1560
tatggtaatc gtgcgagagg gcgcagggac ttcctttgtc ccaaatctgt gcggagccga    1620
aatctgggag gcgccgccgc accccctcta gcgggcgcgg ggcgaagcgg tgcggcgccg    1680
gcaggaagga aatgggcggg gagggccttc gtgcgtcgcc gcgccgccgt ccccttctcc    1740
ctctccagcc tcgggctgt ccgcgggggg acggctgcct tcgggggga cggggcaggg     1800 cggggttcgg cttctggcgt gtgaccggcg gctctagagc ctctgctaac catgttcatg    1860
ccttcttctt tttcctacag ctcctgggca acgtgctggt tattgtgctg tctcatcatt    1920
ttggcaaaga attcgccctt agccccggga gatctttcag cgtgcgttat ggagccgcga    1980
gtcgcagagc tgaagcagaa gattgaggac accttgtgtc cttttggctt cgaagtttat    2040
cccttccagg tggcgtggta caatgaactc ctgcctccag ccttccactt gcccttccca    2100
ggacctaccc tggccttcct ggtactcagc acacctgcta tgtttgacag agccctcaaa    2160
cccttcttaa agagctgcca cttccaaaca ctgagagacc cggtggatca atgtgtgtcc    2220
taccacctga ggagtgttac agagaagttt ccagaagtgc atatggaagt cattgctgac    2280
tatgaggtac accccaatcg gcgacctaag attctcgccc agacagcagc ccatgtggca    2340
ggtgctgctt attactacca acgacaagat gtggatgcag acccatgggg acccagcac    2400 atagcaggtg tgtgcataca ccccgatt ggggctggt ttgccatccg aggggttatg     2460
ttgctgccag ggattgaagt gccaaatttg ccacccagaa agcccctga ctgtgtgcct     2520 acaagagctg gccgcatcac tctgcttgaa ggtttcaatt ccattggcg ggactggact    2580 taccgtgatg ctgtgactcc tgaagaacgg tactccgaag aacagaagat ctacttttcc    2640
accccacctg cccaacgctt ggccctatta ggcttagccc aaccctcaga acaccctagc    2700
actacatctg agcttcctct ttccttgctt actaaacctc agaattccag gagagctcga    2760
agctggctga gtccaagtgt ctcaccacct gtatccccag gccttgatc tcgaggacgg    2820 ggtgaactac gcctgaggat ccgatctttt tccctctgcc aaaaattatg gggacatcat    2880
```

```
gaagcccctt gagcatctga cttctggcta ataaaggaaa tttatttttca ttgcaatagt   2940 gtgttggaat tttttgtgtc tctcactcgg aagcaattcg ttgatctgaa tttcgaccac   3000
ccataatacc cattaccctg gtagataagt agcatggcgg gttaatcatt aactacaagg   3060 aaccccctagt gatggagttg gccactccct ctctgcgcgc tcgctcgctc actgaggccg   3120
ggcgaccaaa ggtcgcccga cgcccgggct tgcccgggc ggcctcagtg agcgagcgag   3180
cgcgcagcct taattaacct aattcactgg ccgtcgtttt acaacgtcgt gactgggaaa   3240
accctggcgt tacccaactt aatcgccttg cagcacatcc ccctttcgcc agctggcgta   3300
atagcgaaga ggcccgcacc gatcgccctt cccaacagtt gcgcagcctg aatggcgaat   3360
gggacgcgcc ctgtagcggc gcattaagcg cggcgggtgt ggtggttacg cgcagcgtga   3420
ccgctacact tgccagcgcc ctagcgcccg ctcctttcgc tttcttccct tcctttctcg   3480
ccacgttcgc cggctttccc cgtcaagctc taaatcgggg gctcccttta gggttccgat   3540
ttagtgcttt acggcacctc gaccccaaaa aacttgatta gggtgatggt tcacgtagtg   3600
ggccatcgcc ctgatagacg gttttttcgcc ctttgacgtt ggagtccacg ttctttaata   3660
gtggactctt gttccaaact ggaacaacac tcaaccctat ctcggtctat tcttttgatt   3720
tataagggat tttgccgatt tcggcctatt ggttaaaaaa tgagctgatt taacaaaaat   3780
ttaacgcgaa ttttaacaaa atattaacgc ttacaattta ggtggcactt tcggggaaa   3840 tgtgcgcgga acccctattt gtttattttt ctaaatacat tcaaatatgt atccgctcat   3900
gagacaataa ccctgataaa tgcttcaata atattgaaaa aggaagagta tgagtattca   3960
acatttccgt gtcgccctta ttcccttttt tgcggcattt tgccttcctg ttttttgctca   4020 cccagaaacg ctggtgaaag taaaagatgc tgaagatcag ttgggtgcac gagtgggtta   4080
catcgaactg gatctcaaca gcggtaagat ccttgagagt tttcgccccg aagaacgttt   4140
tccaatgatg agcactttta aagttctgct atgtggcgcg gtattatccc gtattgacgc   4200
cgggcaagag caactcggtc gccgcataca ctattctcag aatgacttgg ttgagtactc   4260
accagtcaca gaaaagcatc ttacggatgg catgacagta agagaattat gcagtgctgc   4320
cataaccatg agtgataaca ctgcggccaa cttacttctg acaacgatcg gaggaccgaa   4380
ggagctaacc gcttttttgc acaacatggg ggatcatgta actcgccttg atcgttggga   4440
accggagctg aatgaagcca taccaaacga cgagcgtgac accacgatgc ctgtagcaat   4500
ggcaacaacg ttgcgcaaac tattaactgg cgaactactt actctagctt cccggcaaca   4560
attaatagac tggatggagg cggataaagt tgcaggacca cttctgcgct cggcccttcc   4620
ggctggctgg tttattgctg ataaatctgg agccggtgag cgtgggtctc gcggtatcat   4680
tgcagcactg gggccagatg gtaagccctc ccgtatcgta gttatctaca cgacggggag   4740
tcaggcaact atggatgaac gaaatagaca gatcgctgag ataggtgcct cactgattaa   4800
gcattggtaa ctgtcagacc aagtttactc atatatactt tagattgatt taaaacttca   4860
tttttaattt aaaaggatct aggtgaagat cctttttgat aatctcatga ccaaaatccc   4920
ttaacgtgag ttttcgttcc actgagcgtc agaccccgta gaaaagatca aaggatcttc   4980
ttgagatcct ttttttctgc gcgtaatctg ctgcttgcaa acaaaaaaac caccgctacc   5040
agcggtggtt tgtttgccgg atcaagagct accaactctt tttccgaagg taactggctt   5100
cagcagagcg cagataccaa atactgttct tctagtgtag ccgtagttag gccaccactt   5160
caagaactct gtagcaccgc ctacatacct cgctctgcta atcctgttac cagtggctgc   5220
```

| | |
|---|---|
| tgccagtggc gataagtcgt gtcttaccgg gttggactca agacgatagt taccggataa | 5280 |
| ggcgcagcgg tcgggctgaa cgggggggttc gtgcacacag cccagcttgg agcgaacgac | 5340 |
| ctacaccgaa ctgagatacc tacagcgtga gctatgagaa agcgccacgc ttcccgaagg | 5400 |
| gagaaaggcg gacaggtatc cggtaagcgg cagggtcgga acaggagagc gcacgaggga | 5460 |
| gcttccaggg ggaaacgcct ggtatcttta tagtcctgtc gggtttcgcc acctctgact | 5520 |
| tgagcgtcga ttttttgtgat gctcgtcagg ggggcggagc ctatggaaaa acgccagcaa | 5580 |
| cgcggccttt ttacggttcc tggccttttg ctggcctttt gctcacatgt tctttcctgc | 5640 |
| gttatcccct gattctgtgg ataaccgtat taccgccttt gagtgagctg ataccgctcg | 5700 |
| ccgcagccga acgaccgagc gcagcgagtc agtgagcgag gaagcggaag agcgcccaat | 5760 |
| acgcaaaccg cctctccccg cgcgttggcc gattcattaa tgcagctggc acgacaggtt | 5820 |
| tcccgactgg aaagcgggca gtgagcgcaa cgcaattaat gtgagttagc tcactcatta | 5880 |
| ggcaccccag gctttacact ttatgcttcc ggctcgtatg ttgtgtggaa ttgtgagcgg | 5940 |
| ataacaattt cacacaggaa acagctatga ccatgattac gccagattta attaaggcct | 6000 |
| taattag | 6007 |

<210> SEQ ID NO 7
<211> LENGTH: 6005
<212> TYPE: DNA
<213> ORGANISM: Artificial Sequence
<220> FEATURE:
<223> OTHER INFORMATION: AAV with human codon optimized MMACHC

<400> SEQUENCE: 7

| | |
|---|---|
| gctgcgcgct cgctcgctca ctgaggccgc ccgggcaaag cccgggcgtc gggcgacctt | 60 |
| tggtcgcccg gcctcagtga gcgagcgagc gcgcagagag ggagtggcca actccatcac | 120 |
| taggggttcc ttgtagttaa tgattaaccc gccatgctac ttatctacca gggtaatggg | 180 |
| gatcctctag aactatagct agtcgacatt gattattgac tagttattaa tagtaatcaa | 240 |
| ttacggggtc attagttcat agcccatata tggagttccg cgttacataa cttacggtaa | 300 |
| atggcccgcc tggctgaccg cccaacgacc cccgcccatt gacgtcaata atgacgtatg | 360 |
| ttcccatagt aacgccaata gggactttcc attgacgtca atgggtggag tatttacggt | 420 |
| aaactgccca cttggcagta catcaagtgt atcatatgcc aagtacgccc cctattgacg | 480 |
| tcaatgacgg taaatggccc gcctggcatt atgcccagta catgacctta tgggactttc | 540 |
| ctacttggca gtacatctac gtattagtca tcgctattac catggtcgag gtgagcccca | 600 |
| cgttctgctt cactctcccc atctcccccc cctccccacc cccaattttg tatttattta | 660 |
| ttttttaatt attttgtgca gcgatggggg cggggggggg gggggggcgc gcgccaggcg | 720 |
| gggcggggcg gggcgagggg cggggcgggg cgaggcggag aggtgcggcg gcagccaatc | 780 |
| agagcggcgc gctccgaaag tttcctttta tggcgaggcg gcggcggcgg cggccctata | 840 |
| aaaagcgaag cgcgcggcgg gcgggagtcg ctgcgcgctg ccttcgcccc gtgccccgct | 900 |
| ccgccgccgc ctcgcgccgc ccgccccggc tctgactgac cgcgttactc ccacaggtga | 960 |
| gcgggcggga cggcccttct cctccgggct gtaattagcg cttggtttaa tgacggcttg | 1020 |
| tttcttttct gtggctgcgt gaaagccttg aggggctccg gagggccct ttgtgcgggg | 1080 |
| ggagcggctc gggggtgcg tgcgtgtgtg tgtgcgtggg gagcgccgcg tgcggctccg | 1140 |
| cgctgcccgg cggctgtgag cgctgcgggc gcggcgcggg gctttgtgcg ctccgcagtg | 1200 |
| tgcgcgaggg gagcgcggcc ggggcggtg ccccgcggtg cggggggggc tgcgagggga | 1260 |

```
acaaaggctg cgtgcggggt gtgtgcgtgg gggggtgagc aggggtgtg ggcgcgtcgg    1320 tcgggctgca accccccctg cacccccctc cccgagttgc tgagcacggc ccggcttcgg    1380
gtgcggggct ccgtacgggg cgtggcgcgg ggctcgccgt gccggcggg gggtggcggc     1440 aggtgggggt gccgggcggg gcggggccgc ctcgggccgg ggagggctcg ggggagggc     1500 gcggcggccc ccggagcgcc ggcggctgtc gaggcgcggc gagccgcagc cattgccttt    1560
tatggtaatc gtgcgagagg gcgcagggac ttcctttgtc ccaaatctgt gcggagccga    1620
aatctgggag gcgccgccgc accccctcta gcgggcgcgg ggcgaagcgg tgcggcgccg    1680
gcaggaagga aatgggcggg gagggccttc gtgcgtcgcc gcgccgccgt ccccttctcc    1740
ctctccagcc tcggggctgt ccgcgggggg acggctgcct tcgggggga cggggcaggg     1800 cggggttcgg cttctggcgt gtgaccggcg gctctagagc ctctgctaac catgttcatg    1860
ccttcttctt tttcctacag ctcctgggca acgtgctggt tattgtgctg tctcatcatt    1920
ttggcaaaga attcgatatc gccgccacca tggaacctaa agtcgcagaa ctcaagcaga    1980
agatcgagga caccctgtgc ccgttcggat tcgaggtgta cccttttccaa gtggcctggt    2040 acaacgagct cctgccccct gctttccatt tgccactgcc cggtccgact ctcgcgtttc    2100
ttgtgctgtc gaccccgcg atgttcgacc gcgccctcaa gccgttcctg caatcatgtc     2160
atctgcggat gctgaccgat ccggtcgatc agtgcgtggc ctaccacctg ggtcgcgtca    2220
gggaatccct gccggagctt cagatcgaga tcatcgcgga ttacgaagtg cacccaaacc    2280
ggcggcccaa gattctcgcc caaaccgccg cgcacgtggc tggcgccgcc tattactacc    2340
agcgccagga cgtcgaggcg gacccttggg gcaatcagag aatctctgga gtgtgcatcc    2400
acccacggtt cggggatgg ttcgcaattc ggggcgtggt gctgctgccg ggaatcgagg     2460
tgccagactt gcctcctcga aagccccacg actgcgtgcc aactagagcc gatagaattg    2520
ccctgctgga agggttcaac ttccattggc gcgactggac ctaccgggac gctgtgactc    2580
ctcaagaacg ctacagcgaa gaacagaagg cctactttc aactccgccg gcccagcgcc    2640
tggcactcct gggactggcc cagccctccg agaagcctag ctcccctcg ccggacttgc     2700 ccttcaccac cccggccccc aaaaagcccg gcaaccctag ccgggccagg tcctggctgt    2760
ccccgagggt gtccccgcct gcctcccccg gcccttaatg aaagcttctc gaggacgggg    2820
tgaactacgc ctgaggatcc gatctttttc cctctgccaa aaattatggg gacatcatga    2880
agccccttga gcatctgact tctggctaat aaaggaaatt tatttttcatt gcaatagtgt    2940 gttggaattt tttgtgtctc tcactcggaa gcaattcgtt gatctgaatt tcgaccaccc    3000
ataatcccca ttaccctggt agataagtag catggcgggt taatcattaa ctacaaggaa    3060 ccctagtga tggagttggc cactccctct ctgcgcgctc gctcgctcac tgaggccggg     3120
cgaccaaagg tcgcccgacg ccgggctttg cccgggcgg cctcagtgag cgagcgagcg      3180
cgcagcctta ttaacctaa ttcactggcc gtcgttttac aacgtcgtga ctgggaaaac     3240
cctggcgtta cccaacttaa tcgccttgca gcacatcccc ctttcgccag ctggcgtaat    3300
agcgaagagg cccgcaccga tcgcccttcc caacagttgc gcagcctgaa tggcgaatgg    3360
gacgcgccct gtagcggcgc attaagcgcg gcggtgtgg tggttacgcg cagcgtgacc      3420
gctacacttg ccagcgccct agcgcccgct cctttcgctt tcttcccttc ctttctcgcc    3480
acgttcgccg gctttccccg tcaagctcta aatcggggc tcccttaggg ttccgattt      3540 agtgctttac ggcacctcga ccccaaaaaa cttgattagg gtgatggttc acgtagtggg    3600
```

```
ccatcgccct gatagacggt ttttcgccct ttgacgttgg agtccacgtt ctttaatagt    3660
ggactcttgt tccaaactgg aacaacactc aaccctatct cggtctattc ttttgattta    3720
taagggattt tgccgatttc ggcctattgg ttaaaaaatg agctgattta acaaaaattt    3780
aacgcgaatt ttaacaaaat attaacgctt acaatttagg tggcacttt cggggaaatg     3840 tgcgcggaac ccctatttgt ttatttttct aaatacattc aaatatgtat ccgctcatga    3900
gacaataacc ctgataaatg cttcaataat attgaaaaag gaagagtatg agtattcaac    3960
atttccgtgt cgcccttatt cccttttttg cggcattttg ccttcctgtt tttgctcacc    4020
cagaaacgct ggtgaaagta aaagatgctg aagatcagtt gggtgcacga gtgggttaca    4080
tcgaactgga tctcaacagc ggtaagatcc ttgagagttt tcgccccgaa gaacgttttc    4140
caatgatgag cacttttaaa gttctgctat gtggcgcggt attatcccgt attgacgccg    4200
ggcaagagca actcggtcgc cgcatacact attctcagaa tgacttggtt gagtactcac    4260
cagtcacaga aaagcatctt acggatggca tgacagtaag agaattatgc agtgctgcca    4320
taaccatgag tgataacact gcggccaact tacttctgac aacgatcgga ggaccgaagg    4380
agctaaccgc ttttttgcac aacatggggg atcatgtaac tcgccttgat cgttgggaac    4440
cggagctgaa tgaagccata ccaaacgacg agcgtgacac cacgatgcct gtagcaatgg    4500
caacaacgtt gcgcaaacta ttaactggcg aactacttac tctagcttcc cggcaacaat    4560
taatagactg gatggaggcg gataaagttg caggaccact tctgcgctcg gcccttccgg    4620
ctggctggtt tattgctgat aaatctggag ccggtgagcg tgggtctcgc ggtatcattg    4680
cagcactggg gccagatggt aagccctccc gtatcgtagt tatctacacg acggggagtc    4740
aggcaactat ggatgaacga atagacaga tcgctgagat aggtgcctca ctgattaagc     4800
attggtaact gtcagaccaa gtttactcat atatacttta gattgattta aaacttcatt    4860
tttaatttaa aaggatctag gtgaagatcc ttttttgataa tctcatgacc aaaatccctt    4920
aacgtgagtt ttcgttccac tgagcgtcag accccgtaga aaagatcaaa ggatcttctt    4980
gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct acatacctcg ctctgctaat cctgttacca gtggctgctg    5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
acaccgaact gagataccta cagcgtgagc tatgagaaag cgccacgctt cccgaaggga    5400
gaaaggcgga caggtatccg gtaagcggca gggtcggaac aggagagcgc acgagggagc    5460
ttccaggggg aaacgcctgg tatctttata gtcctgtcgg gtttcgccac ctctgacttg    5520
agcgtcgatt tttgtgatgc tcgtcagggg gcggagcct atggaaaaac gccagcaacg     5580
cggccttttt acggttcctg gccttttgct ggccttttgc tcacatgttc tttcctgcgt    5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gacaggtttc    5820
ccgactggaa agcgggcagt gagcgcaacg caattaatgt gagttagctc actcattagg    5880
cacccccagc tttacacttt atgcttccgg ctcgtatgtt gtgtggaatt gtgagcggat    5940
aacaatttca cacaggaaac agctatgacc atgattacgc cagatttaat taaggcctta    6000
```

-continued attag     6005

<210> SEQ ID NO 8
<211> LENGTH: 6044
<212> TYPE: DNA
<213> ORGANISM: Artificial Sequence
<220> FEATURE:
<223> OTHER INFORMATION: AAV with human MMACHC HA

<400> SEQUENCE: 8

```
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120
taggggttcc ttgtagttaa tgattaaccc gccatgctac ttatctacca gggtaatggg     180
gatcctctag aactatagct agtcgacatt gattattgac tagttattaa tagtaatcaa     240
ttacggggtc attagttcat agcccatata tggagttccg cgttacataa cttacggtaa     300
atggcccgcc tggctgaccg cccaacgacc cccgcccatt gacgtcaata atgacgtatg     360
ttcccatagt aacgccaata gggactttcc attgacgtca atgggtggag tatttacggt     420
aaactgccca cttggcagta catcaagtgt atcatatgcc aagtacgccc cctattgacg     480
tcaatgacgg taaatggccc gcctggcatt atgcccagta catgacctta tgggactttc     540
ctacttggca gtacatctac gtattagtca tcgctattac catggtcgag gtgagcccca     600
cgttctgctt cactctcccc atctcccccc cctccccacc cccaattttg tatttattta     660
ttttttaatt attttgtgca gcgatggggg cggggggggg ggggggcgc gcgccaggcg     720
ggcggggcg gggcgagggg cggggcgggg cgaggcggag aggtgcggcg gcagccaatc     780
agagcggcgc gctccgaaag tttccttttg tggcgaggcg gcggcggcgg cggccctata     840
aaaagcgaag cgcgcggcgg gcgggagtcg ctgcgcgctg ccttcgcccc gtgccccgct     900
ccgccgccgc ctcgcgccgc ccgccccggc tctgactgac cgcgttactc ccacaggtga     960
gcgggcggga cggcccttct cctccgggct gtaattagcg cttggtttaa tgacggcttg    1020
tttcttttct gtggctgcgt gaaagccttg aggggctccg ggagggccct ttgtgcgggg    1080
ggagcggctc ggggggtgcg tgcgtgtgtg tgtgcgtggg gagcgccgcg tgcggctccg    1140
cgctgcccgg cggctgtgag cgctgcgggc gcggcgcggg gctttgtgcg ctccgcagtg    1200
tgcgcgaggg gagcgcggcc ggggcggtg ccccgcggtg cgggggggc tgcgagggga    1260
acaaaggctg cgtgcggggt gtgtgcgtgg gggggtgagc aggggtgtg ggcgcgtcgg    1320
tcgggctgca accccccctg cacccccctc cccgagttgc tgagcacggc ccggcttcgg    1380
gtgcggggct ccgtacgggg cgtggcgcgg ggctcgccgt gccgggcggg gggtggcggc    1440
aggtgggggt gccgggcggg gcgggccgc ctcgggccgg ggagggctcg ggggaggggc    1500
gcggcggccc ccggagcgcc ggcggctgtc gaggcgcggc gagccgcagc cattgccttt    1560
tatggtaatc gtgcgagagg gcgcagggac ttcctttgtc ccaaatctgt gcggagccga    1620
aatctgggag gcgccgccgc acccctcta gcgggcgcgg ggcgaagcgg tgcggcgccg    1680
gcaggaagga aatgggcggg gagggccttc gtgcgtcgcc gcgccgccgt cccttctcc    1740
ctctccagcc tcggggctgt ccgcgggggg acggctgcct tcggggggga cggggcaggg    1800
cggggttcgg cttctggcgt gtgaccggcg gctctagagc ctctgctaac catgttcatg    1860
ccttcttctt tttcctacag ctcctgggca acgtgctggt tattgtgctg tctcatcatt    1920
ttggcaaaga attcgatatc gccgccacca tggaacctaa agtcgcagaa ctcaagcaga    1980
```

-continued

```
agatcgagga cacccctgtgc ccgttcggat tcgaggtgta ccctttccaa gtggcctggt    2040
acaacgagct cctgccccct gctttccatt tgccactgcc cggtccgact ctcgcgtttc    2100
ttgtgctgtc gacccccgcg atgttcgacc gcgccctcaa gccgttcctg caatcatgtc    2160
atctgcggat gctgaccgat ccggtcgatc agtgcgtggc ctaccacctg ggtcgcgtca    2220
gggaatccct gccggagctt cagatcgaga tcatcgcgga ttacgaagtg cacccaaacc    2280
ggcggcccaa gattctcgcc caaaccgccg cgcacgtggc tggcgccgcc tattactacc    2340
agcgccagga cgtcgaggcg gacccttggg gcaatcagag aatctctgga gtgtgcatcc    2400
acccacggtt cggggatgg ttcgcaattc ggggcgtggt gctgctgccg ggaatcgagg    2460
tgccagactt gcctcctcga aagccccacg actgcgtgcc aactagagcc gatagaattg    2520
ccctgctgga agggttcaac ttccattggc gcgactggac ctaccgggac gctgtgactc    2580
ctcaagaacg ctacagcgaa gaacagaagg cctacttttc aactccgccg gcccagcgcc    2640
tggcactcct gggactggcc cagccctccg agaagcctag ctcccctcg ccggacttgc    2700 ccttcaccac cccggccccc aaaaagcccg gcaacctag ccgggccagg tcctggctgt    2760
ccccgagggt gtccccgcct gcctcccccg gccctggggg aagctcgtac ccgtatgatg    2820
tgcccgacta cgcctaatga aagcttctcg aggacgggt gaactacgcc tgaggatccg    2880 atcttttttcc ctctgccaaa aattatgggg acatcatgaa gcccttgag catctgactt    2940 ctggctaata aggaaatttt ttttcattg caatagtgtg ttggaatttt ttgtgtctct    3000
cactcggaag caattcgttg atctgaattt cgaccaccca taatacccat taccctggta    3060
gataagtagc atggcgggtt aatcattaac tacaaggaac ccctagtgat ggagttggcc    3120
actccctctc tgcgcgctcg ctcgctcact gaggccgggc gaccaaaggt cgcccgacgc    3180
ccgggctttg cccgggcggc ctcagtgagc gagcgagcgc gcagccttaa ttaacctaat    3240
tcactggccg tcgttttaca acgtcgtgac tgggaaaacc ctggcgttac ccaacttaat    3300
cgccttgcag cacatccccc tttcgccagc tggcgtaata gcgaagaggc ccgcaccgat    3360
cgcccttccc aacagttgcg cagcctgaat ggcgaatggg acgcgccctg tagcggcgca    3420
ttaagcgcgg cgggtgtggt ggttacgcgc agcgtgaccg ctacacttgc cagcgcccta    3480
gcgcccgctc ctttcgcttt cttcccttcc tttctcgcca cgttcgccgg ctttccccgt    3540
caagctctaa atcgggggct ccctttaggg ttccgattta gtgctttacg gcacctcgac    3600
cccaaaaaac ttgattaggg tgatggttca cgtagtgggc catcgccctg atagacggtt    3660
tttcgccctt tgacgttgga gtccacgttc tttaatagtg gactcttgtt ccaaactgga    3720
acaacactca accctatctc ggtctattct tttgatttat aagggatttt gccgatttcg    3780
gcctattggt taaaaaatga gctgatttaa caaaaattta acgcgaattt taacaaaata    3840
ttaacgctta caatttaggt ggcacttttc ggggaaatgt gcgcggaacc cctatttgtt    3900
tattttctta aatacattca aatatgtatc cgctcatgag acaataaccc tgataaatgc    3960
ttcaataata ttgaaaaagg aagagtatga gtattcaaca tttccgtgtc gcccttattc    4020
ccttttttgc ggcatttgc cttcctgttt ttgctcaccc agaaacgctg gtgaaagtaa    4080
aagatgctga agatcagttg ggtgcacgag tgggttacat cgaactggat ctcaacagcg    4140
gtaagatcct tgagagtttt cgccccgaag aacgttttcc aatgatgagc acttttaaag    4200
ttctgctatg tggcgcggta ttatcccgta ttgacgccgg gcaagagcaa ctcggtcgcc    4260
gcatacacta ttctcagaat gacttggttg agtactcacc agtcacagaa aagcatctta    4320
cggatggcat gacagtaaga gaattatgca gtgctgccat aaccatgagt gataacactg    4380
```

```
cggccaactt acttctgaca acgatcggag gaccgaagga gctaaccgct tttttgcaca      4440
acatggggga tcatgtaact cgccttgatc gttgggaacc ggagctgaat gaagccatac      4500
caaacgacga gcgtgacacc acgatgcctg tagcaatggc aacaacgttg cgcaaactat      4560
taactggcga actacttact ctagcttccc ggcaacaatt aatagactgg atggaggcgg      4620
ataaagttgc aggaccactt ctgcgctcgg cccttccggc tggctggttt attgctgata      4680
aatctggagc cggtgagcgt gggtctcgcg gtatcattgc agcactgggg ccagatggta      4740
agccctcccg tatcgtagtt atctacacga cggggagtca ggcaactatg gatgaacgaa      4800
atagacagat cgctgagata ggtgcctcac tgattaagca ttggtaactg tcagaccaag      4860
tttactcata tactttag attgatttaa aacttcattt ttaatttaaa aggatctagg      4920
tgaagatcct ttttgataat ctcatgacca aaatcccta acgtgagttt tcgttccact      4980
gagcgtcaga ccccgtagaa aagatcaaag gatcttcttg agatcctttt tttctgcgcg      5040
taatctgctg cttgcaaaca aaaaaaccac cgctaccagc ggtggtttgt ttgccggatc      5100
aagagctacc aactctttt ccgaaggtaa ctggcttcag cagagcgcag ataccaaata      5160
ctgttcttct agtgtagccg tagttaggcc accacttcaa gaactctgta gcaccgccta      5220
catacctcgc tctgctaatc ctgttaccag tggctgctgc cagtggcgat aagtcgtgtc      5280
ttaccgggtt ggactcaaga cgatagttac cggataaggc gcagcggtcg ggctgaacgg      5340
ggggttcgtg cacacagccc agcttggagc gaacgaccta caccgaactg agatacctac      5400
agcgtgagct atgagaaagc gccacgcttc ccgaagggag aaaggcggac aggtatccgg      5460
taagcggcag ggtcggaaca ggagagcgca cgagggagct tccaggggga aacgcctggt      5520
atctttatag tcctgtcggg tttcgccacc tctgacttga gcgtcgattt ttgtgatgct      5580
cgtcaggggg gcggagccta tggaaaaacg ccagcaacgc ggccttttta cggttcctgg      5640
ccttttgctg ccttttgct cacatgttct ttcctgcgtt atccctgat tctgtggata      5700 accgtattac cgcctttgag tgagctgata ccgctcgccg cagccgaacg accgagcgca      5760
gcgagtcagt gagcgaggaa gcggaagagc gcccaatacg caaaccgcct ctccccgcgc      5820
gttggccgat tcattaatgc agctggcacg acaggtttcc cgactggaaa gcgggcagtg      5880
agcgcaacgc aattaatgtg agttagctca ctcattaggc accccaggct ttacacttta      5940
tgcttccggc tcgtatgttg tgtggaattg tgagcggata caatttcac acaggaaaca      6000 gctatgacca tgattacgcc agatttaatt aaggccttaa ttag                       6044
```

<210> SEQ ID NO 9
<211> LENGTH: 6098
<212> TYPE: DNA
<213> ORGANISM: Artificial Sequence
<220> FEATURE:
<223> OTHER INFORMATION: AAV with human MMACHC 3xFLAG

<400> SEQUENCE: 9

```
gctgcgcgct cgctcgctca ctgaggccgc ccgggcaaag cccgggcgtc gggcgacctt        60
tggtcgcccg gcctcagtga gcgagcgagc gcgcagagag ggagtggcca actccatcac       120 tagggggttcc ttgtagttaa tgattaaccc gccatgctac ttatctacca gggtaatggg     180
gatcctctag aactatagct agtcgacatt gattattgac tagttattaa tagtaatcaa      240
ttacggggtc attagttcat agcccatata tggagttccg cgttacataa cttacggtaa      300
atggcccgcc tggctgaccg cccaacgacc cccgcccatt gacgtcaata atgacgtatg      360
```

```
ttcccatagt aacgccaata gggactttcc attgacgtca atgggtggag tatttacggt    420
aaactgccca cttggcagta catcaagtgt atcatatgcc aagtacgccc cctattgacg    480
tcaatgacgg taaatggccc gcctggcatt atgcccagta catgacctta tgggactttc    540
ctacttggca gtacatctac gtattagtca tcgctattac catggtcgag gtgagcccca    600
cgttctgctt cactctcccc atctccccec cctccccacc cccaattttg tatttattta    660
ttttttaatt attttgtgca gcgatggggg cggggggggg ggggggcgcg cgcgccaggcg   720 gggcggggcg gggcgagggg cggggcgggg cgaggcggag aggtgcggcg gcagccaatc    780
agagcggcgc gctccgaaag tttcctttta tggcgaggcg gcggcggcgg cggccctata    840
aaaagcgaag cgcgcggcgg gcgggagtcg ctgcgcgctg ccttcgcccc gtgccccgct    900
ccgccgccgc ctcgcgccgc ccgccccggc tctgactgac cgcgttactc ccacaggtga    960
gcgggcggga cggcccttct cctccgggct gtaattagcg cttggtttaa tgacggcttg   1020
tttcttttct gtggctgcgt gaaagccttg aggggctccg ggagggccct ttgtgcgggg   1080
ggagcggctc ggggggtgcg tgcgtgtgtg tgtgcgtggg gagcgccgcg tgcggctccg   1140
cgctgcccgg cggctgtgag cgctgcgggc gcggcgcggg gctttgtgcg ctccgcagtg   1200
tgcgcgaggg gagcgcggcc gggggcggtg ccccgcggtg cgggggggggc tgcgagggga   1260 acaaaggctg cgtgcggggt gtgtgcgtgg ggggtgagc aggggtgtg ggcgcgtcgg    1320 tcgggctgca accccccctg cacccccctc cccgagttgc tgagcacggc ccggcttcgg   1380
gtgcggggct ccgtacgggg cgtggcgcgg ggctcgccgt gccggggcgg gggtggcggc   1440
aggtgggggt gccgggcggg gcggggccgc ctcgggccgg ggagggctcg ggggagggggc  1500 gcggcggccc ccggagcgcc ggcggctgtc gaggcgcggc gagccgcagc cattgccttt   1560
tatggtaatc gtgcgagagg gcgcagggac ttcctttgtc ccaaatctgt gcggagccga   1620
aatctgggag gcgccgccgc accccctcta gcgggcgcgg ggcgaagcgg tgcggcgccg   1680
gcaggaagga aatgggcggg gagggccttc gtgcgtcgcc gcgccgccgt ccccttctcc   1740
ctctccagcc tcggggctgt ccgcgggggg acggctgcct tcgggggga cggggcaggg    1800 cggggttcgg cttctggcgt gtgaccgcg gctctagagc ctctgctaac catgttcatg    1860
ccttcttctt tttcctacag ctcctgggca acgtgctggt tattgtgctg tctcatcatt   1920
ttggcaaaga attcgatatc gccgccacca tggaacctaa agtcgcagaa ctcaagcaga   1980
agatcgagga caccctgtgc ccgttcggat tcgaggtgta cccttttccaa gtggcctggt  2040 acaacgagct cctgccccct gctttccatt tgccactgcc cggtccgact ctcgcgtttc   2100
ttgtgctgtc gaccccgcg atgttcgacc gcgccctcaa gccgttcctg caatcatgtc    2160
atctgcggat gctgaccgat ccggtcgatc agtgcgtggc ctaccacctg gtcgcgtca    2220 gggaatccct gccggagctt cagatcgaga tcatcgcgga ttacgaagtg cacccaaacc   2280
ggcggcccaa gattctcgcc caaaccgccg cgcacgtggc tggcgccgcc tattactacc   2340
agcgccagga cgtcgaggcg gacccttggg gcaatcagag aatctctgga gtgtgcatcc   2400
acccacggtt cggggatgg ttcgcaattc ggggcgtggt gctgctgccg ggaatcgagg    2460
tgccagactt gcctcctcga aagccccacg actgcgtgcc aactagagcc gatagaattg    2520
ccctgctgga agggttcaac ttccattggc gcgactggac ctaccgggac gctgtgactc    2580
ctcaagaacg ctacagcgaa gaacagaagg cctactttc aactccgccg gcccagcgcc    2640
tggcactcct gggactggcc cagcccctccg agaagcctag ctcccctcg ccggacttgc    2700 ccttcaccac cccggccccc aaaaagcccg gcaaccctag ccgggccagg tcctggctgt   2760
```

```
ccccgagggt gtccccgcct gcctcccccg gccctggggg ttcctcggac tacaaagatg    2820
acgacgacaa gggagactat aaggacgacg acgataaggg agattacaag gatgacgatg    2880
acaagggcta atgaaagctt ctcgaggacg gggtgaacta cgcctgagga tccgatcttt    2940
ttccctctgc caaaaattat ggggacatca tgaagcccct tgagcatctg acttctggct    3000
aataaaggaa atttattttc attgcaatag tgtgttggaa ttttttgtgt ctctcactcg    3060
gaagcaattc gttgatctga atttcgacca cccataatac ccattaccct ggtagataag    3120
tagcatggcg ggttaatcat taactacaag gaaccctag tgatggagtt ggccactccc     3180
tctctgcgcg ctcgctcgct cactgaggcc gggcgaccaa aggtcgcccg acgcccgggc    3240
tttgcccggg cggcctcagt gagcgagcga gcgcgcagcc ttaattaacc taattcactg    3300
gccgtcgttt tacaacgtcg tgactgggaa accctggcg ttacccaact taatcgcctt     3360
gcagcacatc ccccttcgc cagctggcgt aatagcgaag aggcccgcac cgatcgccct     3420
tcccaacagt tgcgcagcct gaatggcgaa tgggacgcgc cctgtagcgg cgcattaagc    3480
gcggcgggtg tggtggttac gcgcagcgtg accgctacac ttgccagcgc cctagcgccc    3540 gctccttcg ctttcttccc ttccttctc gccacgttcg ccggctttcc ccgtcaagct      3600
ctaaatcggg ggctcccttt agggttccga tttagtgctt tacggcacct cgaccccaaa    3660
aaacttgatt agggtgatgg ttcacgtagt gggccatcgc cctgatagac ggttttcgc     3720 cctttgacgt tggagtccac gttctttaat agtggactct tgttccaaac tggaacaaca    3780 ctcaaccta tctcggtcta ttcttttgat ttataaggga ttttgccgat ttcggcctat     3840
tggttaaaaa atgagctgat ttaacaaaaa tttaacgcga attttaacaa atattaacg    3900 cttacaattt aggtggcact tttcgggga atgtgcgcgg aaccctatt tgtttatttt      3960 tctaaataca ttcaaatatg tatccgctca tgagacaata accctgataa atgcttcaat    4020
aatattgaaa aaggaagagt atgagtattc aacatttccg tgtcgccctt attccctttt    4080
ttgcggcatt ttgccttcct gttttttgctc acccagaaac gctggtgaaa gtaaaagatg   4140
ctgaagatca gttgggtgca cgagtgggtt acatcgaact ggatctcaac agcggtaaga    4200
tccttgagag ttttcgcccc gaagaacgtt ttccaatgat gagcactttt aaagttctgc    4260
tatgtggcgc ggtattatcc cgtattgacg ccgggcaaga gcaactcggt cgccgcatac    4320
actattctca gaatgacttg gttgagtact caccagtcac agaaaagcat cttacggatg    4380
gcatgacagt aagagaatta tgcagtgctg ccataaccat gagtgataac actgcggcca    4440
acttacttct gacaacgatc ggaggaccga aggagctaac cgcttttttg cacaacatgg    4500
gggatcatgt aactcgcctt gatcgttggg aaccggagct gaatgaagcc ataccaaacg    4560
acgagcgtga ccacgatg cctgtagcaa tggcaacaac gttgcgcaaa ctattaactg      4620
gcgaactact tactctagct tcccggcaac aattaataga ctggatggag gcggataaag    4680
ttgcaggacc acttctgcgc tcggcccttc cggctggctg gtttattgct gataaatctg    4740
gagccggtga gcgtgggtct cgcggtatca ttgcagcact ggggccagat ggtaagccct    4800
cccgtatcgt agttatctac acgacgggga gtcaggcaac tatggatgaa cgaaatagac    4860
agatcgctga gataggtgcc tcactgatta agcattggta actgtcagac caagtttact    4920
catatatact ttagattgat ttaaaacttc attttttaatt taaaaggatc taggtgaaga    4980
tcctttttga taatctcatg accaaaatcc cttaacgtga gttttcgttc cactgagcgt    5040
cagaccccgt agaaaagatc aaaggatctt cttgagatcc ttttttctg cgcgtaatct     5100
```

```
gctgcttgca aacaaaaaaa ccaccgctac cagcggtggt ttgtttgccg gatcaagagc    5160
taccaactct ttttccgaag gtaactggct tcagcagagc gcagatacca aatactgttc    5220
ttctagtgta gccgtagtta ggccaccact tcaagaactc tgtagcaccg cctacatacc    5280
tcgctctgct aatcctgtta ccagtggctg ctgccagtgg cgataagtcg tgtcttaccg    5340
ggttggactc aagacgatag ttaccggata aggcgcagcg gtcgggctga acgggggggtt    5400 cgtgcacaca gcccagcttg gagcgaacga cctacaccga actgagatac ctacagcgtg    5460
agctatgaga aagcgccacg cttcccgaag ggagaaaggc ggacaggtat ccggtaagcg    5520
gcagggtcgg aacaggagag cgcacgaggg agcttccagg gggaaacgcc tggtatcttt    5580
atagtcctgt cgggtttcgc cacctctgac ttgagcgtcg atttttgtga tgctcgtcag    5640
gggggcggag cctatggaaa aacgccagca acgcggcctt tttacggttc ctggccttttt   5700 gctggccttt tgctcacatg ttctttcctg cgttatcccc tgattctgtg gataaccgta    5760
ttaccgcctt tgagtgagct gataccgctc gccgcagccg aacgaccgag cgcagcgagt    5820
cagtgagcga ggaagcggaa gagcgcccaa tacgcaaacc gcctctcccc gcgcgttggc    5880
cgattcatta atgcagctgg cacgacaggt ttcccgactg gaaagcgggc agtgagcgca    5940
acgcaattaa tgtgagttag ctcactcatt aggcaccccca ggctttacac tttatgcttc    6000
cggctcgtat gttgtgtgga attgtgagcg gataacaatt tcacacagga aacagctatg    6060
accatgatta cgccagattt aattaaggcc ttaattag                            6098
```

<210> SEQ ID NO 10
<211> LENGTH: 841
<212> TYPE: DNA
<213> ORGANISM: Mus musculus
<220> FEATURE:
<221> NAME/KEY: misc_feature
<223> OTHER INFORMATION: wild-type mouse Mmachc

<400> SEQUENCE: 10

```
atggagccgc gagtcgcaga gctgaagcag aagattgagg acaccttgtg tccttttggc     60
ttcgaagttt atcccttcca ggtggcgtgg tacaatgaac tcctgcctcc agccttccac    120
ttgcccttcc caggacctac cctggccttc ctggtactca gcacacctgc tatgtttgac    180
agagccctca aacccttctt aaagagctgc cacttccaaa cactgagaga cccggtggat    240
caatgtgtgt cctaccacct gaggagtgtt acagagaagt tccagaagt gcatatggaa    300 gtcattgctg actatgaggt acaccccaat cggcgaccta agattctcgc ccagacagca    360
gcccatgtgg caggtgctgc ttattactac caacgacaag atgtggatgc agacccatgg    420
gggacccagc acatagcagg tgtgtgcata cacccccgat tgggggctg gtttgccatc    480 cgaggggtta tgttgctgcc agggattgaa gtgccaaatt tgccacccag aaagcccct    540 gactgtgtgc ctacaagagc tggccgcatc actctgcttg aaggtttcaa tttccattgg    600
cgggactgga cttaccgtga tgctgtgact cctgaagaac ggtactccga agaacagaag    660
atctactttt ccaccccacc tgcccaacgc ttggccctat taggcttagc ccaaccctca    720
gaacacccta gcactacatc tgagcttcct ctttccttgc ttactaaacc tcagaattcc    780
aggagagctc gaagctggct gagtccaagt gtctcaccac ctgtatcccc aggcccttga    840
t                                                                    841
```

<210> SEQ ID NO 11
<211> LENGTH: 885
<212> TYPE: DNA

<213> ORGANISM: Artificial Sequence
<220> FEATURE:
<223> OTHER INFORMATION: human codon-optimized MMACHC with linker and HA

<400> SEQUENCE: 11

```
atggaaccta aagtcgcaga actcaagcag aagatcgagg acaccctgtg cccgttcgga      60
ttcgaggtgt acccctttcca agtggcctgg tacaacgagc tcctgccccc tgctttccat    120
ttgccactgc ccgtccgac tctcgcgttt cttgtgctgt cgaccccgc gatgttcgac       180
cgcgccctca agccgttcct gcaatcatgt catctgcgga tgctgaccga tccggtcgat    240
cagtgcgtgg cctaccacct gggtcgcgtc agggaatccc tgccggagct tcagatcgag    300
atcatcgcgg attacgaagt gcacccaaac cggcggccca agattctcgc caaaccgcc    360
gcgcacgtgg ctggcgccgc ctattactac cagcgccagg acgtcgaggc ggacccttgg    420
ggcaatcaga gaatctctgg agtgtgcatc cacccacggt tcggggatg gttcgcaatt     480
cggggcgtgg tgctgctgcc gggaatcgag gtgccagact gcctcctcg aaagccccac    540
gactgcgtgc caactagagc cgatagaatt gccctgctgg aagggttcaa cttccattgg    600
cgcgactgga cctaccggga cgctgtgact cctcaagaac gctacagcga agaacagaag    660
gcctactttt caactccgcc ggcccagcgc ctggcactcc tgggactggc ccagccctcc    720
gagaagccta gctccccctc gccggacttg cccttcacca ccccggcccc caaaaagccc    780
ggcaaccccta gccgggccag gtcctggctg tccccgaggg tgtccccgcc tgcctccccc    840
ggccctgggg gaagctcgta cccgtatgat gtgcccgact acgcc                     885
```

<210> SEQ ID NO 12
<211> LENGTH: 939
<212> TYPE: DNA
<213> ORGANISM: Artificial Sequence
<220> FEATURE:
<223> OTHER INFORMATION: human codon-optimized MMACHC with linker and 3xFLAG

<400> SEQUENCE: 12

```
atggaaccta aagtcgcaga actcaagcag aagatcgagg acaccctgtg cccgttcgga      60
ttcgaggtgt acccctttcca agtggcctgg tacaacgagc tcctgccccc tgctttccat    120
ttgccactgc ccgtccgac tctcgcgttt cttgtgctgt cgaccccgc gatgttcgac       180
cgcgccctca agccgttcct gcaatcatgt catctgcgga tgctgaccga tccggtcgat    240
cagtgcgtgg cctaccacct gggtcgcgtc agggaatccc tgccggagct tcagatcgag    300
atcatcgcgg attacgaagt gcacccaaac cggcggccca agattctcgc caaaccgcc    360
gcgcacgtgg ctggcgccgc ctattactac cagcgccagg acgtcgaggc ggacccttgg    420
ggcaatcaga gaatctctgg agtgtgcatc cacccacggt tcggggatg gttcgcaatt     480
cggggcgtgg tgctgctgcc gggaatcgag gtgccagact gcctcctcg aaagccccac    540
gactgcgtgc caactagagc cgatagaatt gccctgctgg aagggttcaa cttccattgg    600
cgcgactgga cctaccggga cgctgtgact cctcaagaac gctacagcga agaacagaag    660
gcctactttt caactccgcc ggcccagcgc ctggcactcc tgggactggc ccagccctcc    720
gagaagccta gctccccctc gccggacttg cccttcacca ccccggcccc caaaaagccc    780
ggcaacccta gccgggccag gtcctggctg tccccgaggg tgtccccgcc tgcctccccc    840
ggccctgggg gttcctcgga ctacaaagat gacgacgaca aggagacta taaggacgac    900
gacgataagg gagattacaa ggatgacgat gacaagggc                           939
```